US008483476B2

(12) United States Patent
Bardos et al.

(10) Patent No.: US 8,483,476 B2
(45) Date of Patent: Jul. 9, 2013

(54) PHOTOVOLTAIC CELL MANUFACTURING

(75) Inventors: Robert Andrew Bardos, North Bondi (AU); Thorsten Trupke, Coogee (AU)

(73) Assignee: BT Imaging Pty Ltd, Sydney (AU)

( * ) Notice: Subject to any disclaimer, the term of this patent is extended or adjusted under 35 U.S.C. 154(b) by 611 days.

(21) Appl. No.: 12/675,642

(22) PCT Filed: Sep. 1, 2008

(86) PCT No.: PCT/AU2008/001297
§ 371 (c)(1),
(2), (4) Date: Feb. 26, 2010

(87) PCT Pub. No.: WO2009/026661
PCT Pub. Date: Mar. 5, 2009

(65) Prior Publication Data
US 2011/0188733 A1    Aug. 4, 2011

(30) Foreign Application Priority Data

Aug. 30, 2007 (AU) ................. 2007904706

(51) Int. Cl.
G06K 9/00 (2006.01)
(52) U.S. Cl.
USPC .......................................... 382/149; 382/145
(58) Field of Classification Search
USPC ............... 382/149, 145, 141; 438/8, 16, 800, 438/67, 66, 64, 57; 356/300, 302, 72, 237.1–237.6, 394; 250/582, 493.1; 427/5
See application file for complete search history.

(56) References Cited

U.S. PATENT DOCUMENTS

| | | |
|---|---|---|
| 2009/0051914 A1 | 2/2009 | Trupke et al. |
| 2009/0206287 A1 | 8/2009 | Trupke et al. |
| 2010/0025598 A1 | 2/2010 | Short et al. |

FOREIGN PATENT DOCUMENTS

| | | |
|---|---|---|
| GB | 2231958 | 11/1990 |
| JP | 2007067102 | 3/2007 |
| WO | WO 2005/080950 | 9/2005 |
| WO | WO 2007/041758 | 4/2007 |
| WO | WO 2008/037002 | 4/2008 |
| WO | WO 2008/052237 | 5/2008 |

OTHER PUBLICATIONS

International Search Report mailed Nov. 14, 2008 in corresponding Australian Application No. PCT/AU2008/001297, 5 pages.

*Primary Examiner* — Tri T Ton
(74) *Attorney, Agent, or Firm* — Fish & Richardson P.C.

(57) ABSTRACT

Disclosed is a method (300) of manufacturing at least one semiconductor photovoltaic cell or module and for classifying semiconductor material. In one implementation (500) the method involves luminescence imaging a wafer at each of a plurality of stages (312-324) of the manufacturing process, and comparing at least two images obtained from the imaging step in respect of the same wafer to identify the incidence or growth of a manufacturing process induced fault. The wafer is removed (351-356) from the manufacturing process (310) where a process induced fault is identified that exceeds a predetermined level of acceptability or the fault may be remedied, or the wafer passed to an alternate manufacturing process to match its characteristics. In an alternate implementation the method comprises classifying semiconductor material. For example, providing at least two wafers, obtaining luminescence images of each wafer comparing the images to determine the electrical structure similarity of the wafers, and grouping wafers with a predetermined level of electrical structure similarity into the same family. The inventive method is suitable for determining various forms of mechanical, electrical and cosmetic irregularities.

38 Claims, 18 Drawing Sheets

PHOTOVOLTAIC CELL MANUFACTURING

FIELD OF THE INVENTION

The present invention relates generally to the manufacture of silicon wafers, photovoltaic cells and photovoltaic cell modules and, in particular, to problems and faults that arise in producing the silicon wafers from source material and in the manufacture of photovoltaic cells and modules. In the case of silicon photovoltaic cells, this problem is most significant when multicrystalline silicon is used for photovoltaic cell manufacture. However, the problem is also evident, and the arrangements disclosed herein may be used, in single crystal silicon photovoltaic cell manufacture. The invention is not limited to the detection of cracks. Cracks are an economically significant example of a manufacturing process induced fault. Other faults, such as localised shunting (caused for example by metal "spiking through" the p-n junction) or wafer contamination may also be detected by this method.

Any discussion of the prior art throughout the specification should in no way be considered as an admission that such prior art is widely known or forms part of common general knowledge in the field.

BACKGROUND

The manufacture of photovoltaic cells and photovoltaic cell modules using a particular semiconductor technology, such as silicon wafer technology, involves a number of stages. During silicon wafer manufacture, photovoltaic cell manufacture and photovoltaic cell module manufacture, faults may be introduced into the wafer, finished cell or module which are difficult to detect by standard optical inspection methods used for manufacturing quality control. Further, pre-existing faults can grow during the photovoltaic cell and module manufacture steps and can result in a significant damage of the wafer during photovoltaic cell manufacture or of the finished photovoltaic cell during module manufacture or, potentially, after the module has been installed and is subject to physical stress such as day/night thermal cycling. Whilst cracks for instance may develop at any stage, possibly the worst case is where such cracks or other faults do not result in significant degradation of the electrical output at the final electrical testing stage of photovoltaic cell manufacture, but when such a cell incorporating a crack is formed into a photovoltaic cell module together with other photovoltaic cells, a breakage then occurs. This can ruin not just the particular wafer concerned, but the entire photovoltaic cell module. Thus the formation of cracks or other faults and their possible growth through the processing and manufacture stages of silicon wafers, photovoltaic cells, and subsequent manufacture of photovoltaic cell modules using such cells, is a significant problem.

A worldwide shortage of silicon is forcing photovoltaic cell manufactures to decrease the thickness of wafers. This can increase the rate of cell breakage due to crack creation and growth.

It is an object of the present invention to overcome or ameliorate at least one of the disadvantages of the prior art, or to provide a useful alternative.

SUMMARY

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

In a broad aspect, the present invention provides a method of manufacturing at least one semiconductor photovoltaic device, said method comprising the steps of:

obtaining a plurality of images of at least one semiconductor wafer associated with at least one stage of a semiconductor photovoltaic device manufacturing process;

comparing at least two of the images to identify the incidence or growth of a fault; and determining whether such incidence or growth of a fault identified exceeds a predetermined level of acceptability.

Preferably the images are luminescence images. These images allow the identification of the incidence or growth of a fault, particularly a process induced fault, to determine whether the wafer is of sufficient quality to remain the process. If, however, the incidence or growth of the fault exceeds a predetermined level of acceptability, an operator may discard the wafer, may determine that the fault needs to be rectified and/or may return the wafer for further manufacturing.

The at least two images may be images of a single wafer taken at different positions in the manufacturing process, for example, before and/or after a stage of the manufacturing process. Alternatively, the at least two images are images taken at a position of the manufacturing process, the images being those of two wafers sufficiently similar in electrical structure. Such two wafers are preferably classified as originating from the same source material for example wafers that were originally adjacent and consecutively derived from the same source material.

In an alternative embodiment, the imaging may be conducted on a single wafer before and/or after a stage of the manufacturing process.

The method as described above provides a reliable mechanism for determining whether the wafer has faults which may cause poor performance of a resulting photovoltaic cell or module.

The faults which can be identified by the present application include any mechanical, electrical and even cosmetic faults in the wafer, photovoltaic cell or photovoltaic module. In particular, the process can locate a crack, shunt or contamination of a silicon wafer.

The imaging can be conducted at any point in the manufacturing process from when the wafer is first produced, ie by sawing from the block of source material or by extrusion.

The processes may also be used for determining statistics of fault incidence and/or growth associated with respective stages of the photovoltaic cell manufacturing process. As will be appreciated by persons skilled in the art this technique is very useful for assessing the level of performance of the respective stage and if necessary providing remedial action to the stage.

It will also be appreciated by persons skilled in the art that the imaging may be performed at particular stages in the manufacturing process or throughout the process. In particular imaging may be conducted at at least the following stages of the manufacturing process:

(i) prior to commencement of the manufacture;
(ii) immediately after the wafer is produced from the source material;
(iii) after initial saw damage etch of the wafer;
(iv) between initial saw damage etch and emitter diffusion;
(v) between emitter diffusion and silicon nitride deposition;
(vi) between silicon nitride deposition and screen printing of metal contacts on the wafer;

(vii) between screen printing of metal contacts on the wafer and thermal treatment of the wafer;

(viii) on completion of the photovoltaic cell manufacture and before incorporation of the photovoltaic cell into a photovoltaic cell module.

In a second aspect, the present invention provides a method of analysing a manufacturing process for photovoltaic cells and modules, said process comprising:

obtaining a plurality of images of at least one semi-conductor wafer associated with at least one stage of a semiconductor photovoltaic cell or module manufacturing process, comparing at least two of the images to identify the incidence or growth of a fault in said wafer at a particular stage of the manufacturing process, and collating data of fault incidence or growth associated with the respective stage of the manufacturing process, and optionally applying remedial action to said stage.

In a third aspect, the present invention provides a manufacturing system for a photovoltaic device having a plurality of stages by which a silicon wafer is formed from a source material and processed to form a photovoltaic cell or module, said system comprising:

an imaging apparatus configured to capture a plurality of images of a wafer prior to and during said manufacturing process, a processor configured compare and analyse at least two of said images to identify the incidence or growth of a fault in the wafer and determine whether said fault exceeds a predetermined level of acceptability.

The imaging of wafers is photoluminescence (PL) imaging, although electroluminescence (EL) imaging at steps subsequent to the formation of metal contacts on the wafer (ie. actual formation of a photovoltaic cell) may also be used. For finished cells, EL is possible and cheaper, although PL usually gives a somewhat better result. For cells in modules, EL is more practical and cheaper. These monitoring arrangements have particular application where the photovoltaic cell is being manufactured from multi-crystalline silicon where cracks are not readily discernable amongst the large amount of structure arising in PL or EL images from electrically active crystal grain boundaries, crystal grains of highly variable electrical quality and regions of poor electrical quality due for example to crystal defects or impurities. Nevertheless, with single crystal cells, the same process may be applied as PL imaging can readily show the existence of cracks as dark lines, owing to enhanced electron-hole recombination which occurs at the crack.

As mentioned above, photoluminescent (PL) and/or electroluminescence (EL) imaging may be used with the present method.

PL imaging is typically used to record an image of each raw multi-crystalline wafer after it is produced and as it enters the photovoltaic cell production facility or process. Similar PL images are recorded after some or all of the subsequent manufacturing steps, up to and including one or more PL (or EL) image taken at steps subsequent to the formation of metal contacts on the wafer. Automated comparison of the initial PL image (or subsequent PL images) with PL or EL images taken after at least one further processing step can be used to reveal the presence of faults e.g. additional dark lines which may be attributed to cracking. Cracking is an important example of a "process induced defect"—i.e. a defect induced by the manufacturing process. The occurrence of a defect in a particular wafer or cell may depend on variation or error in the manufacturing steps as well as variation in the material characteristics making some wafers more liable to suffer a process induced defect. In the case of cracking, the multicrystalline character of the material is highly variable so even a highly reproducible manufacturing step will have a variable outcome. Statistical analysis of the correlation between the number, length and spatial distribution of cracks and other process induced defects and the likelihood of eventual breakage may then be obtained and used to develop algorithms for the rejection of wafers from the production line.

In addition, such statistical analysis allows an operator to analyse the manufacturing process and provide remedial action by way of feed forward or feed back control to assist in efficient and reliable manufacture of the wafers, photovoltaic cells and photovoltaic modules.

Other aspects of the invention are also disclosed.

BRIEF DESCRIPTION OF THE DRAWINGS

Some aspects of the prior art and one or more embodiments of the present invention will now be described with reference to the drawings and appendices, in which.

DETAILED DESCRIPTION INCLUDING BEST MODE

The present invention is described in the following embodiments using luminescence imaging however it would be understood by persons skilled in the art that other forms of imaging may be applicable.

In addition, the present invention allows for the identification of incidence or growth of various faults. The following embodiments describe the identification of cracks in particular but other faults such as shunts, contamination, etc are within the scope It has recently been identified that PL imaging may be used to provide measurements of the spatially resolved electronic characteristics of silicon wafers or photovoltaic cells, in particular, the local minority carrier lifetime and the local separation of the quasi-fermi levels.

The present disclosure proposes that luminescence imaging may be used to identify the incidence and/or growth of faults during one or more stages of photovoltaic cell manufacture and production.

PL imaging and EL imaging detect the existence of cracks through a reduction in the PL or EL signal in the region immediately surrounding the crack. This reduction occurs because the crack creates an internal boundary (semiconductor/air boundary or semiconductor/vacuum boundary for example) and such a discontinuity of the bulk semiconductor crystal is of low electrical quality, resulting in enhanced charge carrier (electron-hole) recombination occurring at the crack surfaces. Charge carriers from the regions immediately surrounding the crack diffuse towards the crack surfaces, significantly reducing the density of one or both polarity of charge carriers (electrons and holes) in these regions. Since the PL or EL signal from a particular region depends on the product of the electron and hole density in that region, the PL or EL signal originating from the regions immediately surrounding the crack is decreased significantly. In an EL image or PL image of an otherwise featureless wafer, a crack will appear as a feature with relatively low EL or PL respectively. The feature will have a similar shape to the physical structure of the crack, but with a width greater than the physical width of the crack owing to the reduction of the EL or PL signal from the regions immediately surrounding the crack.

Figure 1:
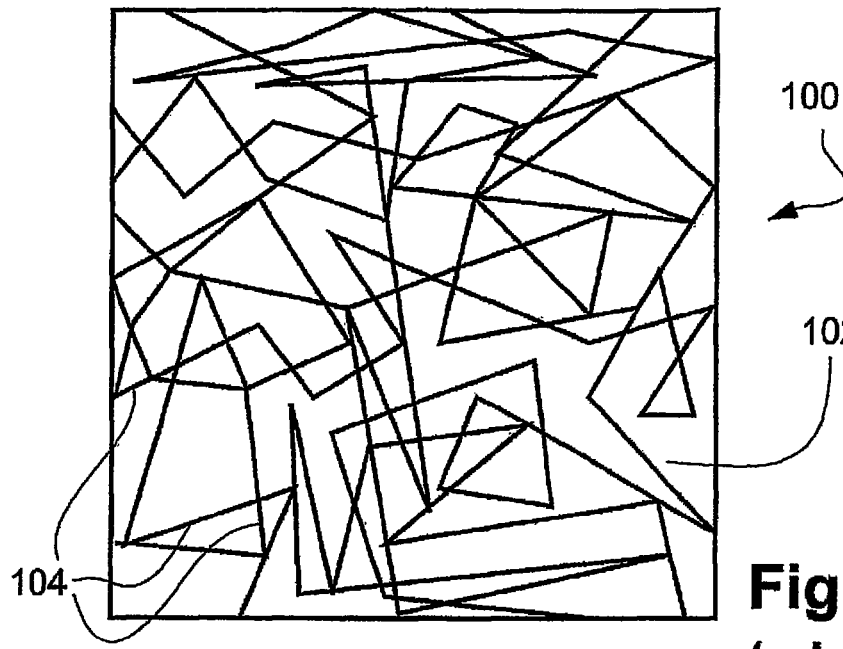
FIG. 1 illustrates a wafer of multicrystalline silicon useful for photovoltaic cell manufacture and the grain boundaries present therein.

FIG. 1 schematically illustrates a multi-crystalline silicon wafer 100 that may be used for the formation of a silicon photovoltaic cell. Silicon photovoltaic cells may alternatively be formed from single crystal silicon wafers, such processes usually incurring a higher capital cost for the raw silicon wafer material, but also revealing greater efficiencies in terms of electrical production. Multi-crystalline wafer manufacture typically, but not exclusively, involves the creation of large ingots which, as of 2007, can have dimensions of up to approx 0.8 metres×0.8 metres×0.4 metres and weigh hundreds of kilograms. The trend is towards even larger ingots. Ingots may be created by the casting of molten silicon into a crucible. Alternatively, the starting silicon material is melted in the crucible and (upon cooling) crystallization of the melt occurs, forming the ingot. Ingot formation can even occur without a crucible, in a process called Electromagnetic Casting. The ingots are then cut into rectangular blocks having a generally square transverse cross-section. Each block is then sawn, cut or otherwise derived into slices to define a wafer to be processed to form a photovoltaic cell.

In an alternative embodiment wafers can be produced by extruding the semiconductor materials more suitable dye Wafers at this stage may include a process induced defect or fault arising from their production e.g. separation of wafers from the ingot, by sawing, cutting, or similar processes applied to the ingot to form blocks or bricks, and then to the blocks or bricks to form wafers.

Such a wafer 100 is seen in FIG. 1 to be generally square and includes an edge 102 and a number of grain boundaries 104 dispersed throughout the wafer 100. Where a wafer is sourced from some other process, a shape other than square may arise. The grain boundaries 104 may represent surfaces of lower electrical quality than intra-grain regions due to the presence of electrically active crystal defects at the grain boundaries. However the reduction in electrical quality at grain boundaries is highly variable, even within a single wafer, and the electrical quality of separate grains is also highly variable due to the variable segregation of crystal defects and impurities between neighbouring grains during crystal growth and processing to form a photovoltaic cell. In addition to grain boundaries of poor electrical quality, other localised regions of poor electrical quality, such as crystal defect or impurity rich regions, also commonly occur in multi-crystalline material, which can lead to highly variable electrical quality within individual grains. Grain boundaries may be at normal incidence to the surface, or at any other angle, and may or may not be readily discerned with the eye depending on the surface preparation of the wafer and the nature of the particular grain boundary. Whilst the grain boundaries 104 may be visible they nevertheless represent a mechanical connection between adjacent boundaries in the silicon wafer.

The existence of such grain boundaries or other crystal defect or impurity rich regions is distinct from the incidence of cracks that can form in the wafer 100 and which represent a small separation of the crystal(s) and which ultimately can cause failure of a photovoltaic cell formed from such a wafer. Cracks may form entirely internally or terminate on the edge of the wafer.

Currently, the production of the wafer either by sawing, cutting, etc, source material or by extrusion, costs around a third of the total cost of producing a photovoltaic device. Accordingly, the present invention is also particularly suitable for recognising faults in wafers prior to their introduction to the cell manufacturing process shown in FIG. 3 and, as discussed later, classification of these wafers into "families" of wafers which originate from the same source.

Figure 2:
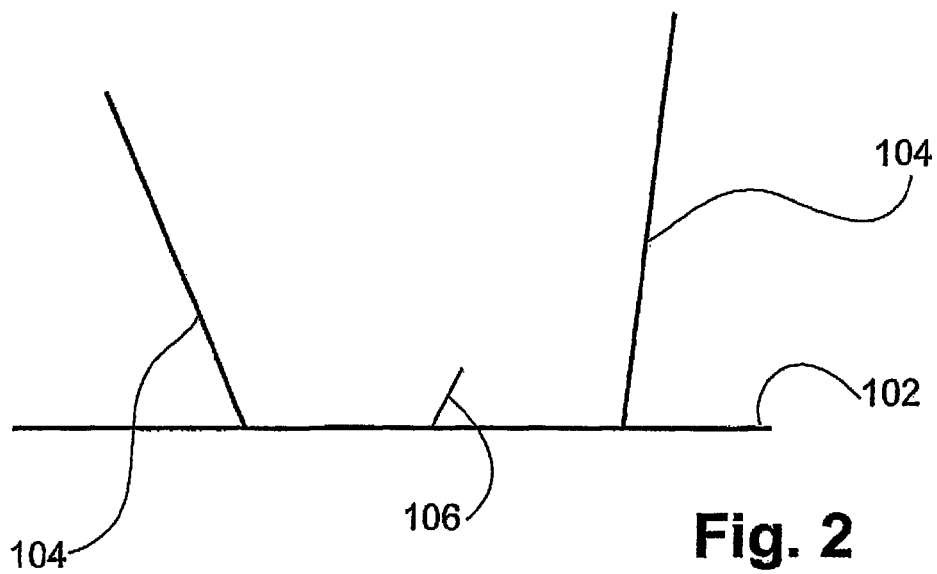
FIG. 2 is a detailed view of a portion of the wafer of FIG. 1 showing a crack.

FIG. 2 shows an enlarged representation of the edge 102 of the wafer 100 where a number of the grain boundaries 104 are seen to extend to the edge 102. Also seen extending inwardly from the edge 102 is a crack 106 that may not be visible to the unaided human eye or using a conventional optical inspection method. Cracks may be entirely internal or, as illustrated, terminate on the edge of the wafer. The crack 106 may be present in the wafer 100 after initial production and before processing into a photovoltaic cell, or may develop during the photovoltaic cell or photovoltaic cell module processing stages, of which there are a number. Further, such a crack 106 may be small and may not affect the overall wafer 100 throughout its entire life. As an alternative, the crack 106 may grow over time, particularly through handling and the various processing stages, or during module assembly, but also through thermal expansion and contraction when the wafer is in use as a photovoltaic cell as part of a photovoltaic cell module. In a worse case scenario, the crack may grow to form a significant crack which can then separate an entire section of the wafer 100 from the remainder thus destroying the particular photovoltaic cell formed therefrom, and perhaps making completely unserviceable a photovoltaic cell module incorporating such a wafer.

Figure 3:
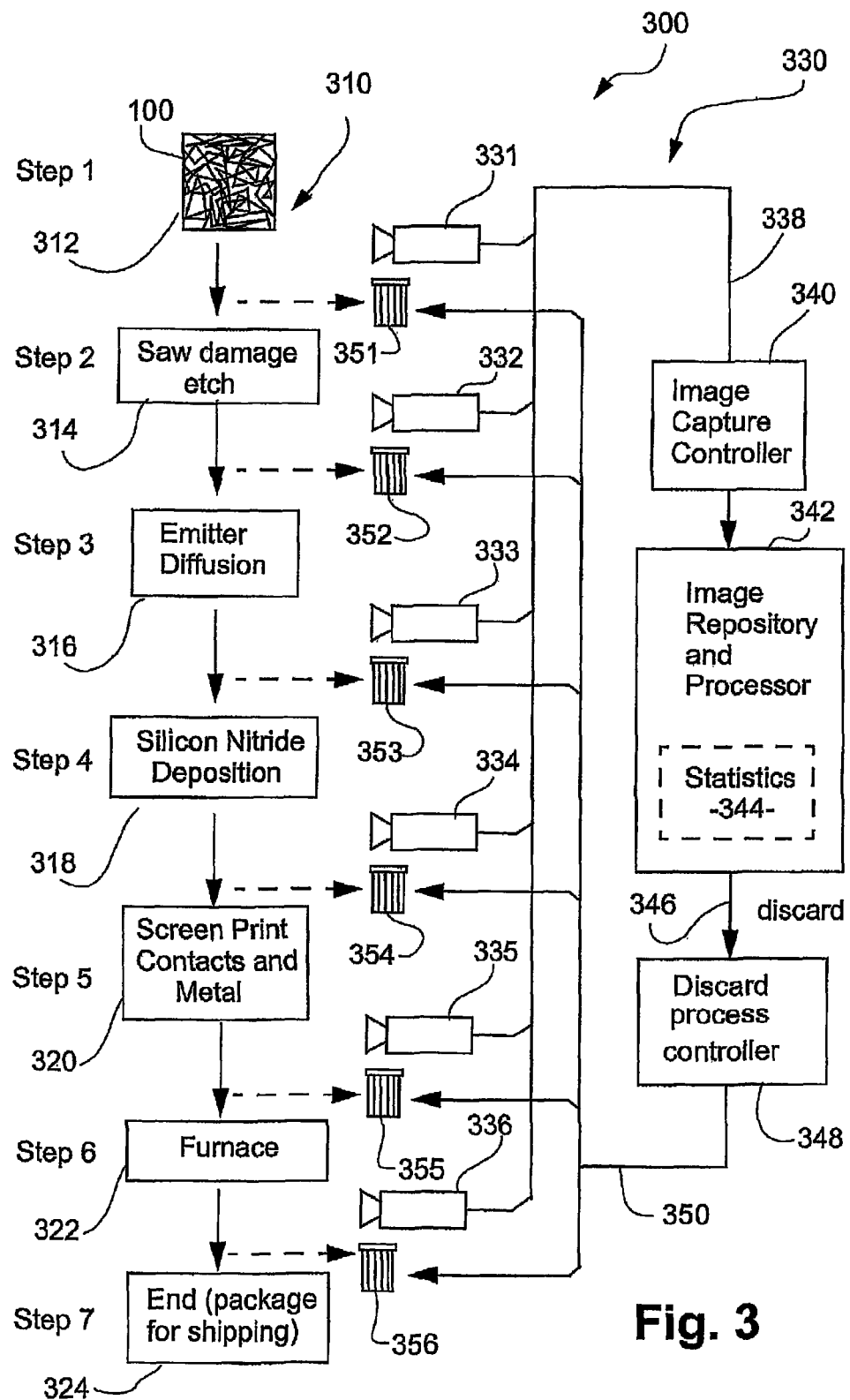
FIG. 3 schematically illustrates a photovoltaic cell manufacturing system and process according to one aspect of the present disclosure.

FIG. 3 shows a representation 300 of a photovoltaic cell manufacturing process 310 and an imaging system 330 which may be used to assess individual wafers for the presence and/or growth of faults including cracks. The process 310 and any of its stages may result in the creation or growth of process induced faults or defects.

The photovoltaic cell manufacturing process 310 is represented as a relatively generic series of seven steps (step 1-step 7). In a first step 312, a silicon wafer 100, (preferably of multi-crystalline silicon) is received. The wafer 100 may have been manufactured at a separate manufacturing plant or facility and transported to the photovoltaic cell manufacturing process 310. Alternatively, wafer fabrication may be performed within the same facility. In a second step 314, the wafer 100 is typically saw damage etched. In the third step 316, emitter diffusion is performed on the wafer to dope the wafer to form the necessary P-N junction. A fourth step 318 involves a silicon nitride deposition on the wafer 100 and a fifth step 320 involves the screen printing of a silver loaded paste to form the grid and busbars on the front of the wafer. The fifth step 320 also involves the screen printing of silver loaded paste to form solderable busbars on the rear of the wafer and screen printing of aluminium loaded paste over the remaining area of the rear side of the wafer, typically overlapping with the silver busbars. The metal contacts so formed are used to efficiently extract current from the cells and to make connections between individual wafers 100 to form a photovoltaic cell module.

In a sixth step 322, the wafer is thermally treated, typically by being fired in a furnace, in order to sinter the screen printed metal loaded paste as well as passivate electrically active defects in the silicon through gettering from the aluminium and hydrogenation from the (hydrogen containing) silicon nitride layer. An alternate thermal treatment is known as rapid thermal processing. In a final step 324, the process 310 ends typically with the processed photovoltaic cell wafer 100 being packaged for shipping or transferred to a module manufacturing facility.

Although not illustrated, some manufacturing processes include additional steps between the sixth step 322 and the final step 324. One additional step is where edge isolation, for example by laser scribing, is carried out. In this step, a laser is used to create an isolation grove which cuts through the emitter layer of the cell, isolating most of the cell area from the edge of the cell which is of poor electrical quality, and may also provide a shunt path through the overlapping of relatively heavily doped diffused layers of opposite type (i.e. p-type or n-type) which form the p-n junction and the ohmic contact of the photovoltaic cell. In a further additional step, the cell is electrically tested.

This step necessarily imposes mechanical stress on the cell and may lead to crack creation or growth.

The process 310 described above is generally representative of most photovoltaic cell manufacturing processes that use multicrystalline silicon wafers. Further, the various steps 312-322 as described are most generalised and may be adapted according to the specific form of manufacturing implemented in any particular facility or process. Further, each of the steps may be broken down into a number of sub-steps peculiar to the particular manufacturing process. Nevertheless, each of the steps represents a significant stage at which the particular wafer being processed may be inspected according to the present disclosure for the presence and/or growth of cracks or other faults. Other stages of alternate processes may also be used. Also, in the process 310, wafers are processed to form photovoltaic cells. The imaging arrangements to be described may operate at any one or more stages of the process 310 either upon wafers, as they are considered at the early stages of the process 310, or upon cells, as the wafers may be considered at later stages of the process 310. Accordingly, unless expressly noted, a reference to a wafer in the following description and associated claims may be considered also a reference to a cell, and in some cases a completed module.

As also seen in FIG. 3, the imaging system 330 is configured to image the wafer 100 at or between (before or after, or both before and after) certain ones of the manufacturing steps 312-324. The inventive process provides a mechanism for identifying the incidence in growth of any mechanical, electrical or cosmetic fault in the wafer, cell or module as it is subjected to the manufacturing process 310. As illustrated, an imaging arrangement comprising a photoluminescence camera 331-336 is provided between each of the 7 stages of manufacture illustrated. In a specific implementation, the final camera 336 in the system 330 may be an electroluminescence (EL) camera or involve combined EL and PL imaging. In another specific implementation, one or more cameras in the system 330, placed at one or more of step 6 or subsequent steps, may be an electroluminescence (EL) camera or involve combined EL and PL imaging. Each of the cameras 331-336 are connected to an image capture controller 340 via a connection 338 for the capturing of images of each wafer 100 being processed, at each stage of processing. The image capture controller 340 delivers the captured images to an image repository and processor 342. The repository and processor 342 maintains track of each wafer 100 as it passes through the process 310 so that images captured at any stages may be subsequently compared with one or more previous images for the same wafer 100 for the identification of cracks and/or the growth of cracks.

For example, the PL camera 331 is configured to obtain an image of a wafer 100 upon arrival at the factory and at commencement of the process 310, which is stored in the repository 342 under control of the controller 340. After the saw damage etch step 314, the camera 332 captures a further image of the same wafer 100, with this image also being stored in the repository 342. In a specific implementation when the saw damage etch step 314 is performed, the image captured by PL camera 332 is compared with the image captured by the PL camera 331 by the processor 342. Where a crack is seen to have developed and/or grown and such is deemed to be beyond a predetermined acceptable limit, the processor 342 can issue a discard signal 346 to a discard process controller 348. The discard process controller 348 outputs a signal 350 to a respective one of a number of automated discarding mechanisms 351-356 (schematically represented in FIG. 3 as garbage bins) associated with a corresponding one of the cameras 331-336 so that the specific wafer 100 may be discarded at the relevant stage at which a crack was identified to be beyond acceptable limits. At this particular stage of the process 310, the discard mechanism 352 would be actuated. Alternatively, it may be possible to take the "discarded" wafer and pass it to a repair station, or another manufacturing process where the wafer is within acceptable production limits ie less expensive/cheaper photovoltaic device manufacture.

If the wafer 100 passes through emitter diffusion 316, the camera 333 obtains a further image. Where the wafer 100 proceeds through the remaining stages of the process 310, corresponding images may be captured by the corresponding cameras 333-336. At each stage, an image comparison is desirably performed to assess the wafer 100 for viability with a view to discarding via the corresponding discard mechanism 353-356, if found unacceptable.

Because of the multi-crystalline nature of the wafer 100, the identification of cracks, even using PL imaging, may be difficult. In this fashion, simply capturing a single PL image of the wafer to identify any such crack may not be a viable approach. This is because of the multiplicity of spatial features in a typical PL image of a multi-crystalline wafer which may be indistinguishable from a crack, or obscure a crack. This necessitates comparison of images before and after process steps to determine the introduction of a crack or the increase in size of an existing crack. Spatial features may include edges, lines, grain boundaries and dislocation lines.

In one particular implementation, each time a new image of a particular wafer in the process 310 is obtained, that image may then be compared with each previous image of the particular wafer captured in the process 310 in order to identify any changes of significance. It may be the case that the difference between any two images captured at consecutive stages within the process 310 is not significant for identification, whereas a comparison between a current image and an image taken, for example 2, 3 or 4 steps prior, may be sufficient to invoke discarding of the wafer 100. It is desirable that discarding of the wafer 100 occur at the stage or time a significant crack is identified. This will aid in optimising the process 310 to avoid performing later process stages upon wafers that would otherwise be discarded in any event. This technique will also aid in the optimisation of the production process by ensuring consistent feedback on the faults induced by the process. Such information may then be used in a statistical manner to apply remedial action, if required, to the various stages of the manufacturing process.

As shown in FIG. 3, a PL imaging device and an associated discarding mechanism may be formed between each processing stage so that crack affected wafers are not passed onto any subsequent stages. Depending upon the particular manufacturing facility in which the process 310 is being implemented, it is not essential that imaging and discarding be performed at each and every stage. Further, it is not essential that a discarding mechanism 351-356 be associated with each corresponding imaging system 331-336. In this regard, some of the stages of the process 310 may be suitable for imaging, but not discarding. Crack data obtained at that stage may nevertheless be used to assess possible discarding at a later stage. Typically, PL or EL imaging takes approximately 1 second per wafer and thus is relatively quick in the manufacturing process. This speed of capture, coupled with associated speed of image processing performed by the processor 342, can enable the system 330 to be implemented between each manufacturing stage. However, where a particular stage is not found to historically provide significant incidence of cracks or their growth, monitoring at such a stage may be omitted in order to reduce cost and/or speed up the manufacturing process. It may be, in some implementations, that imaging and possible discarding of wafers need only be performed between 2 or 3 of the stages of the process 310. For processes that use many more stages, the extent to which the system is implemented may be dependent upon a statistical history for the relevant production line.

To this end, the processor 342 desirably incorporates a statistics module 344 which can maintain a record of the incidence of cracks and/or their growth throughout the various stages of the process 310. From those statistics, it may be determined, for example, that the development or growth of cracks in the saw damage etch step 314 is not significant. As a consequence, the PL camera 332 and discarding mechanism 352 may be omitted from such a system in order to obtain the better efficiency or reduce cost. Similarly, the statistics may indicate that the silicon nitride deposition step 318 has little or no influence upon the creation or growth of cracks and similarly the camera 334 and discarding mechanism 352 may also be omitted.

As each manufacturing facility will have its own peculiarities of manufacture in terms of quality, particularly at individual stages, in a typical implementation, each of the imaging devices and discarding arrangements may be incorporated at the major steps in manufacturing until such time as reliable statistics are obtained for the particular plant. Once those statistics are obtained and analysed, certain ones of the imaging and discarding arrangements may be omitted to further optimise the system 300.

In FIG. 3, the imaging system 330 is shown to include a separate image capture controller 340, repository and processor 342 and discard process controller 348. This representation may be physical or functional. In the latter, each of the functions 340, 342 and 348 may be performed in a computer system 400, such as that shown in FIG. 4 wherein parts of the processes of FIGS. 3, 5 and 6 may be implemented as software, such as one or more application programs executable within the computer system 400. Specifically, the cameras 331-335 and discard mechanisms 351-355 may interface to the computer 400 via a network 422 or directly via input/output (I/O) interfaces 408. In particular, the processes of FIGS. 3, 5 and 6 may effected, at least in part, by instructions in the software that are carried out within the computer system 400. The instructions may be formed as one or more code modules, each for performing one or more particular tasks. The software may also be divided into two separate parts, in which a first part and the corresponding code modules performs the imaging and image processing and a second part and the corresponding code modules manage a user interface between the first part and a user, such as an operator of the system 300. The software may be stored in a computer readable medium, including the storage devices described below, for example. The software is loaded into the computer system 400 from the computer readable medium, and then executed by the computer system 400. A computer readable medium having such software or computer program recorded on it is a computer program product. The use of the computer program product in the computer system 400 preferably effects an advantageous apparatus for the testing of wafers prior to and during photovoltaic cell manufacture.

Figure 4:
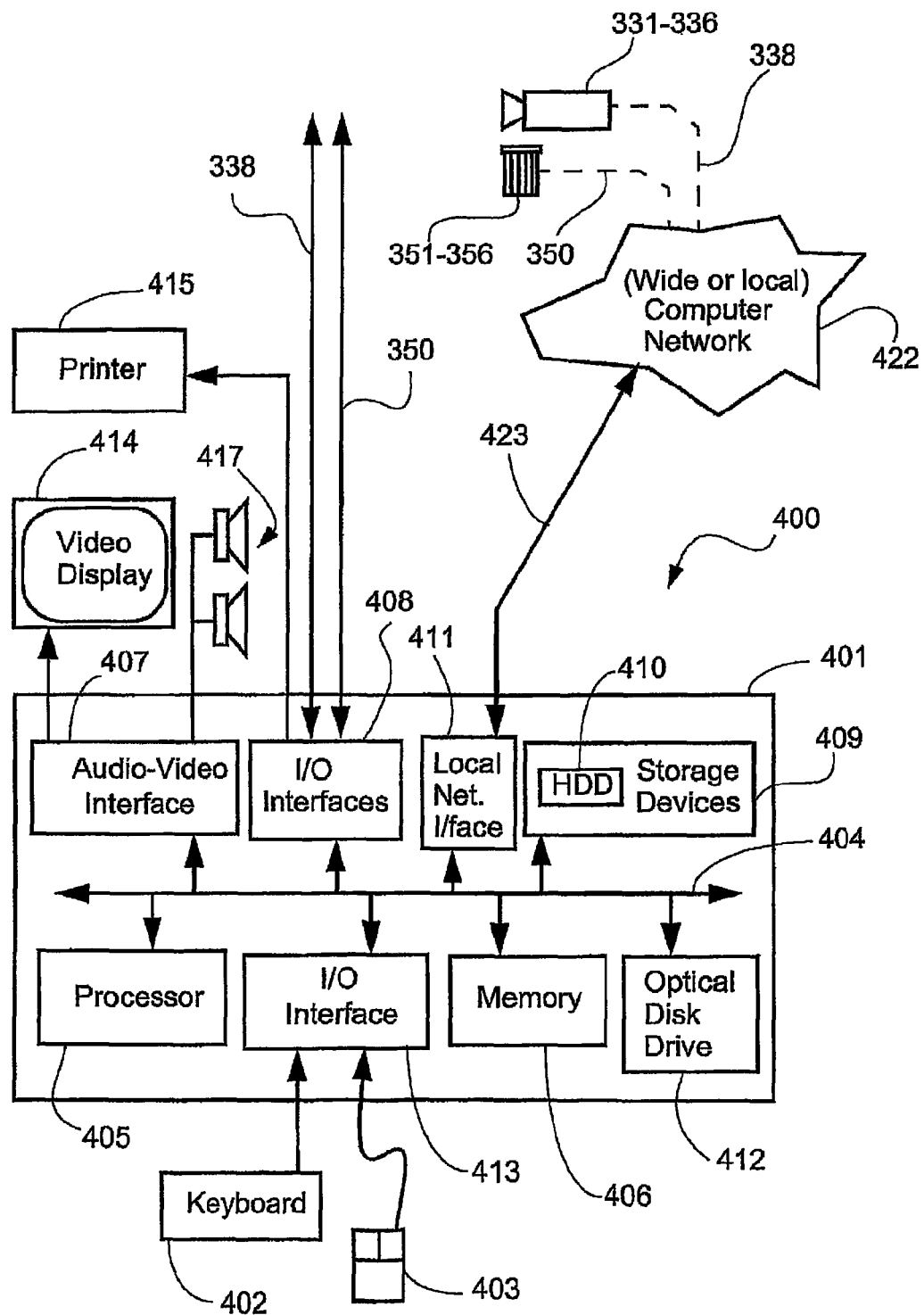
FIG. 4 is a schematic block diagram of a general purpose computer useful for control of the system and process of FIG. 3.

As seen in FIG. 4, the computer system 400 is formed by a computer module 401, user input devices such as a keyboard 402 and a mouse pointer device 403, and output devices including a printer 415, a display device 414 and loudspeakers 417. A network interface 411 is provided for interfacing the computer module 401 to the computer network 422, which may be a local network forming part of a control system for the system 300 and process 310. Such may also or alternatively be a wide network such as the Internet or World Wide Web permitting remote control or monitoring of the process 310.

The computer module 401 typically includes at least one processor unit 405, and a memory unit 406 for example formed from semiconductor random access memory (RAM) and read only memory (ROM). The module 401 also includes an number of input/output (I/O) interfaces including an audio-video interface 407 that couples to the video display 414 and loudspeakers 417, an I/O interface 413 for the keyboard 402 and mouse 403 and optionally a joystick (not illustrated). The interface 408 may be used for connecting the printer 415. As noted above, the interface 408 may also be configured to directly couple to each of the cameras 331-335 and discard mechanisms 351-355. This may involve use of a specific imaging or control interface. The computer module 401 also includes a local network interface 411 which couples, via a connection 423, to the computer network 422.

The interfaces 408 and 413 may afford both serial and parallel connectivity, the former typically being implemented according to the Universal Serial Bus (USB) standards and having corresponding USB connectors (not illustrated). Analog connectivity in the interface 408 may be used where the cameras 331-335 are directly connected. Storage devices 409 are provided and typically include a hard disk drive (HDD) 410. Other devices such as a floppy disk drive and a magnetic tape drive (not illustrated) may also be used. An optical disk drive 412 is typically provided to act as a non-volatile source of data. Portable memory devices, such optical disks (eg: CD-ROM, DVD), USB-RAM, and floppy disks for example may then be used as appropriate sources of data to the system 400.

The components 405 to 413 of the computer module 401 typically communicate via an interconnected bus 404 and in a manner which results in a conventional mode of operation of the computer system 400 known to those in the relevant art. Examples of computers on which the described arrangements can be practised include IBM-PC's and compatibles, Sun Sparcstations, Apple Mac™ or alike computer systems evolved therefrom.

Typically, the application programs discussed above are resident on the hard disk drive 410 and read and controlled in execution by the processor 405. Intermediate storage of such programs and any data fetched from the network 422 may be accomplished using the semiconductor memory 406, possibly in concert with the hard disk drive 410. In some instances, the application programs may be supplied to the user encoded on one or more CD-ROM and read via the corresponding drive 412, or alternatively may be read by the user from the networks 420 or 422. Still further, the software can also be loaded into the computer system 400 from other computer readable media. Computer readable media refers to any storage medium that participates in providing instructions and/or data to the computer system 400 for execution and/or processing. Examples of such media include floppy disks, magnetic tape, CD-ROM, a hard disk drive, a ROM or integrated circuit, a magneto-optical disk, or a computer readable card such as a PCMCIA card and the like, whether or not such devices are internal or external of the computer module 401. Examples of computer readable transmission media that may also participate in the provision of instructions and/or data include radio or infra-red transmission channels as well as a network connection to another computer or networked device, and the Internet or Intranets including e-mail transmissions and information recorded on Websites and the like.

The second part of the application programs and the corresponding code modules mentioned above may be executed to implement one or more graphical user interfaces (GUIs) to be rendered or otherwise represented upon the display 414. Through manipulation of the keyboard 402 and the mouse 403, a user of the computer system 400 and the application may manipulate the interface to provide controlling commands and/or input to the applications associated with the GUI(s). Desirably the image processing and comparison applications (to be described) run autonomously without need for specific user control, and thus integrate with the manufacturing process 310 essentially seamlessly.

The methods of wafer testing, and examination may alternatively be implemented in dedicated hardware such as one or more integrated circuits performing the functions or sub functions of image comparison, to be described. Such dedicated hardware may include graphic processors, digital signal processors, or one or more microprocessors and associated memories.

Figure 5:
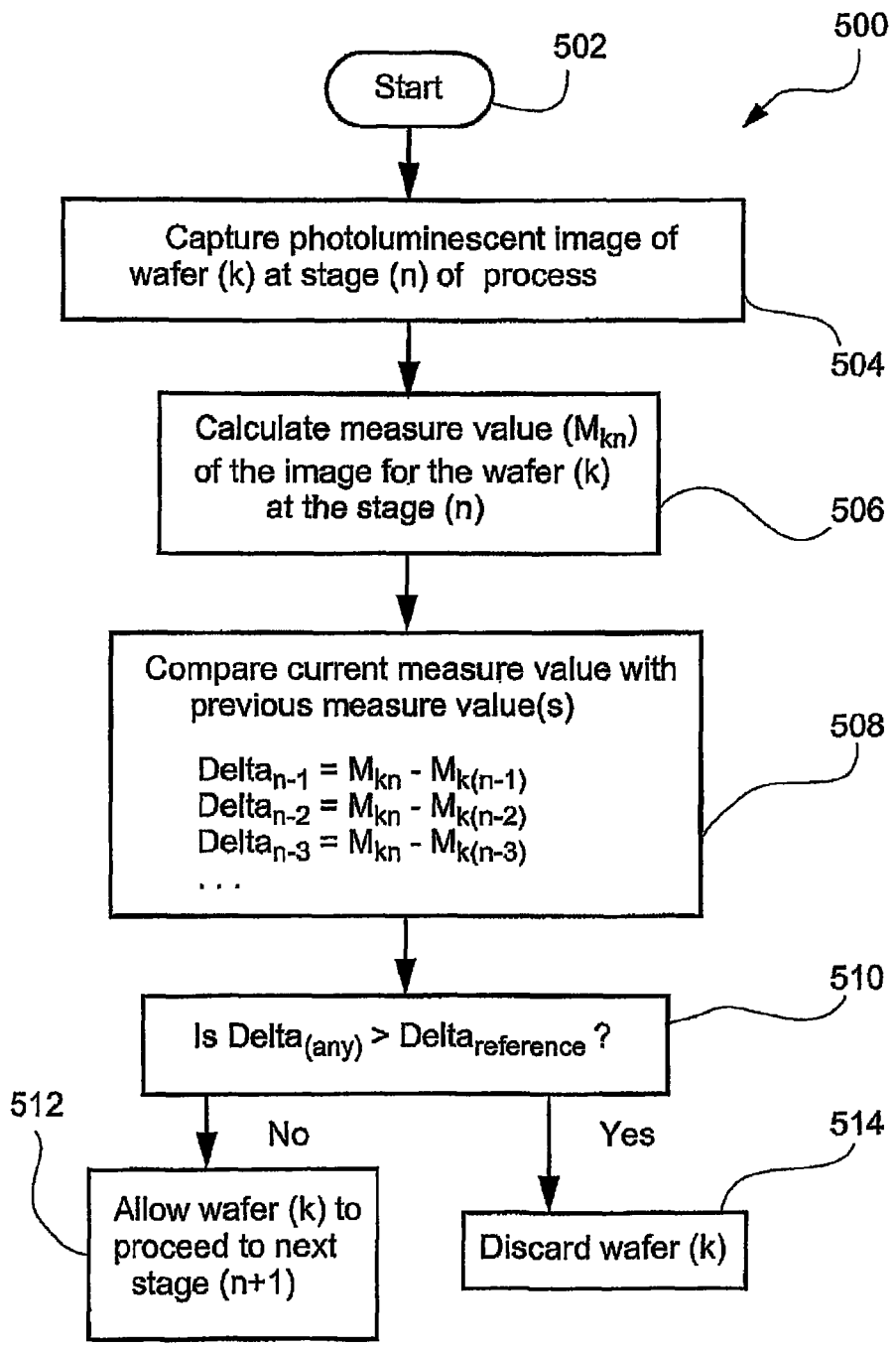
FIG. 5 is a flowchart of image processing used in the process and system of FIG. 3.

FIG. 5 shows an imaging method 500 performed by the system 330 and particularly the processor 342 for the processing of various images captured by the cameras 331-336 to test the wafers 100. The method 500 is desirably performed by executing software in the systems 400 and 300 (FIGS. 4 and 3 respectively) and commences at step 502 followed by a step 504 in which a photo-luminescent image of a particular wafer (k) is obtained at a stage (n) of the photovoltaic cell manufacturing process. In almost all implementations, the stage (n) will at least include the final stage 322 of the process 310. In step 506, a measure value ($M_{kn}$) is determined from the image of the wafer (k) at the particular stage (n).

At step 508, a current measure value for the particular wafer in question is then compared with previous measure values for the same wafer. This stage is relevant where at least two imaging stages have been performed and is used to develop a "delta" value relating to the difference in the measured value between the two stages. That difference can be indicative of the creation or growth of a crack between the stages. At step 510, the delta value at any one of the determined stages is then compared with a reference delta value representing a maximum threshold value for an acceptable wafer. Where the delta value of the particular wafer in question exceeds the reference value, step 514 follows and the processor 342 emits the "discard" signal 346 to discard or divert the wafer (k) at step 514 from the process 310. Where the delta value is less than the reference value at step 510, step 512 follows to allow the wafer (k) to proceed to the next stage (n+1) of the process 310.

In the circumstance where there is no prior image or measure value to compare (as occurs at the first stage 312 where the first image is captured by the PL camera 331), an alternate process may be performed substituting for steps 506 and 508 merely to identify the presence of a crack. The alternate process may involve use of a specific imaging system designed to detect cracks. Such a system may be used at the start of the manufacturing process 310. Such systems typically cannot be used for multiple purposes. By contrast, PL imaging can be used for monitoring a variety of wafer characteristics, not just cracks. If that crack, of itself, is deemed to exceed acceptable limits, discarding via the discard arrangement 351 may then be performed.

Figure 6:
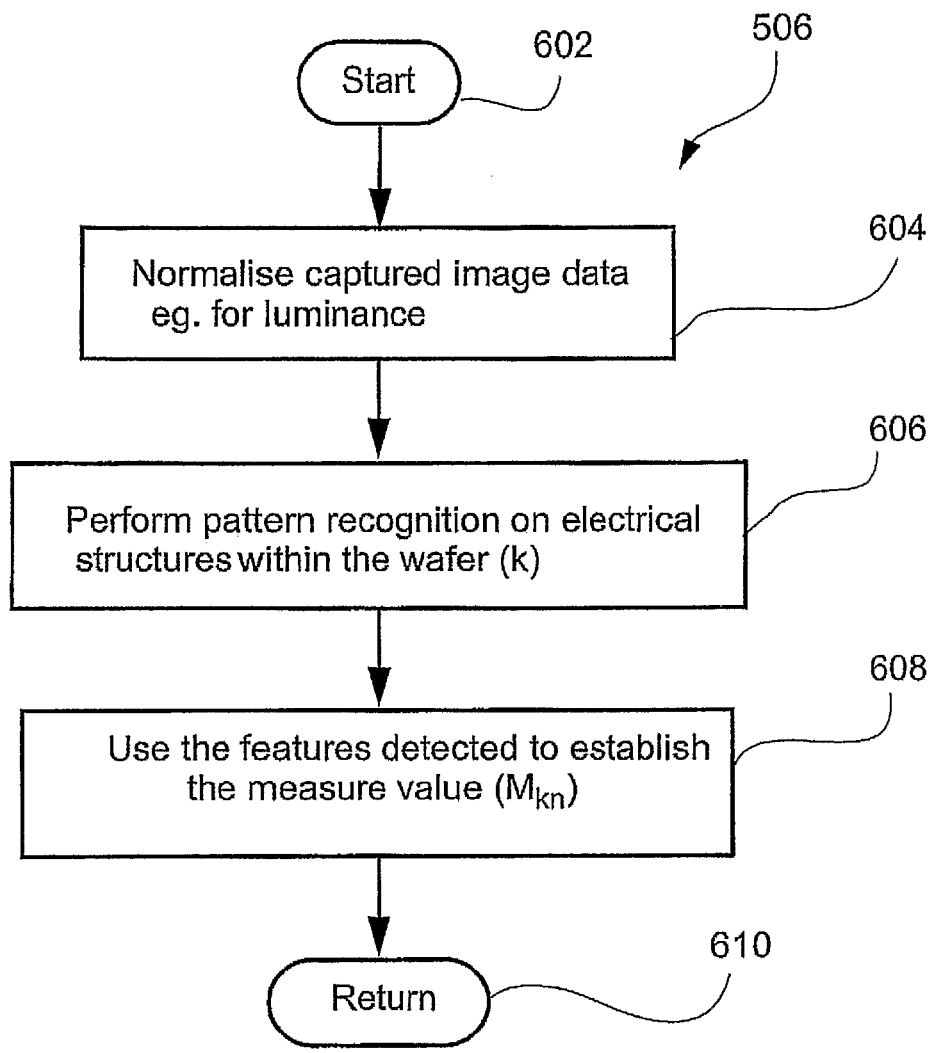
FIG. 6 is a flowchart of the calculation of the measure value step of FIG. 5.

FIG. 6 shows detail of a process for the step 506. This sub routine includes an entry step 602 and then a step 604 whereby the captured image data is normalised. This is used to permit comparison between values obtained from different stages and to accommodate imaging differences between the cameras 331-335. At step 606, pattern recognition is then performed on the electrical structures found within the wafer (k). The electrical structures within the wafer 100 may be lines due to electrically active crystal grain boundaries (grain boundaries seen in FIG. 1), edges due to crystal grains of highly variable electrical quality and lines and edges due to regions of poor electrical quality arising for example from crystal defects or impurities or lines in various configurations including "crosshair" configurations formed by cracks (eg: 106 seen in FIG. 2). From the features detected in step 606, a measure value ($M_{kn}$) for the particular wafer (k) at stage (n) may be determined in step 608. The measure value may also be used to assess any correlation of number, length and spatial distribution of cracks, and how such may change between processing stages. The sub-routine returns in step 610.

Figure 21:
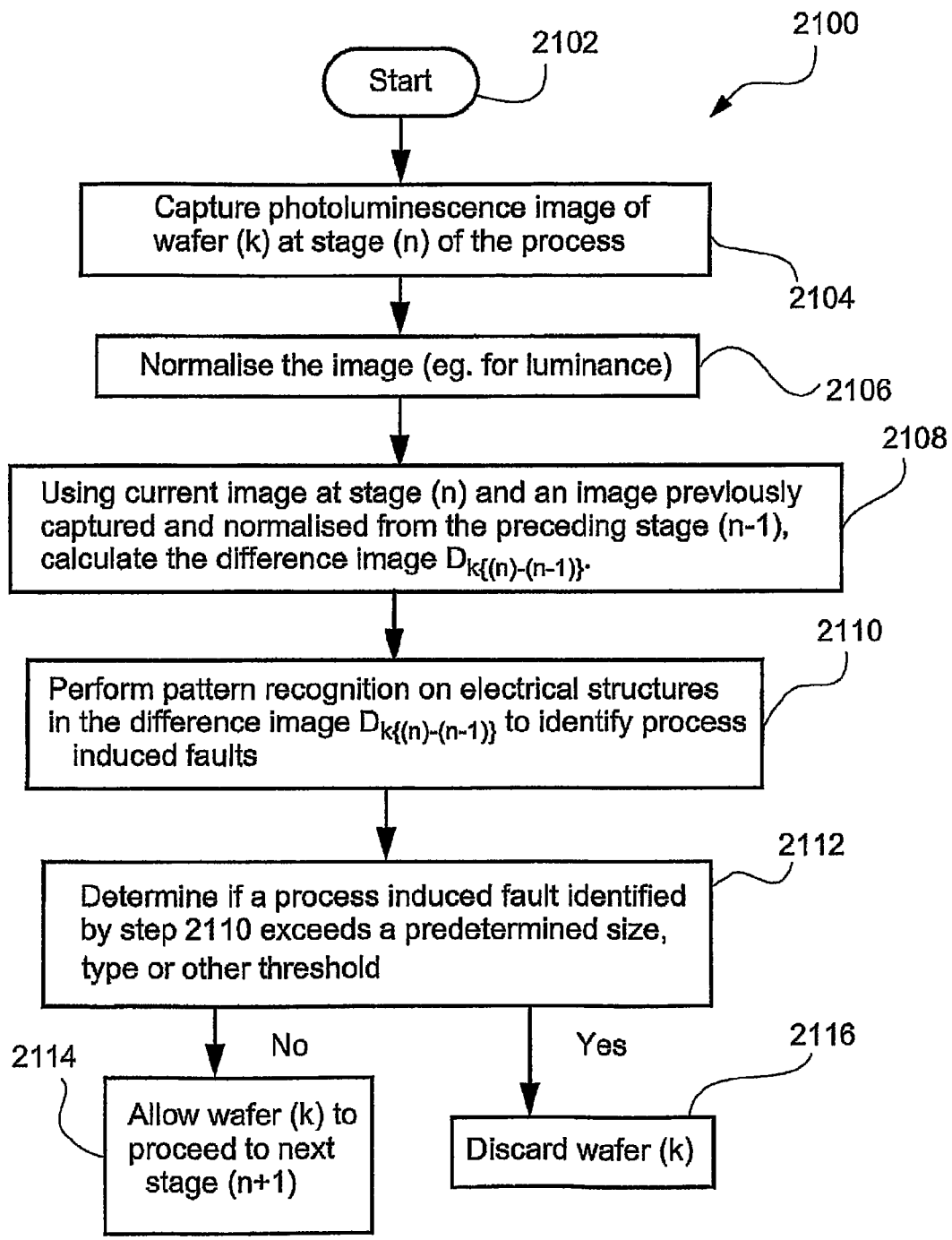
FIG. 21 shows an alternate imaging method applicable to the system of FIG. 3.

FIG. 21 shows an alternate imaging method 2100 that may be performed by the system 330 and particularly the processor 342 for the processing of various images captured by the cameras 331-336 to test the wafers 100. The method 2100 is desirably performed by executing software in the systems 400 and 300 and commences at step 2102 followed by a step 2104 in which a photoluminescence image of a particular wafer (k) is obtained at a stage (n) of the photovoltaic cell manufacturing process. In almost all implementations, the stage (n) will at least include the final stage 322 of the process 310. In step 2106, the photoluminescence image is normalised. Using the image from step 2106 and an image previously captured and normalised from the preceding stage (n−1), a difference image $D_{k\{(n)\_-(n-1)\}}$ is calculated in step 2108. In step 2110 pattern recognition on electrical structures in the difference image $D_{k\{(n)-(n-1)\}}$ is performed to identify process induced faults. In step 2112 the results of step 2110 are compared with predetermined thresholds for the size, type or other aspect of process induced faults. In steps 2114 and 2116 the wafer is allowed to proceed to the next stage, or rejected, respectively.

Figure 7:
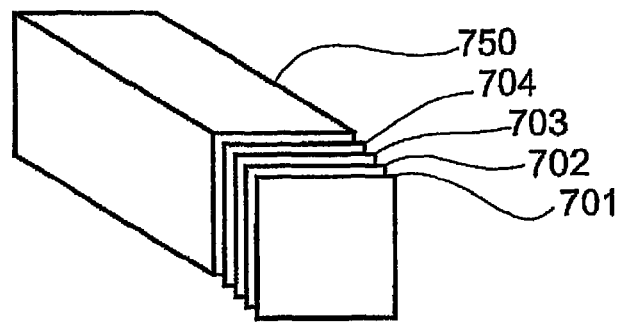
FIG. 7 shows how features of multicrystalline silicon relate amongst adjacent wafers in a cassette.

An alternate image processing arrangement to identify process induced faults, such as cracks, derives from an understanding that when the wafers are sawn from the blocks, they are then typically loaded into a cassette or other receptacle for storage and transportation prior to photovoltaic processing. Moreover, as seen in FIG. 7, the wafers 701, 702, 703 and 704 are loaded into the cassette in the same, consecutive or sequential, order in which they are sawn from the block 750. Accordingly, with the exception of waste represented by the thickness of the saw cut, the wafers in the cassette emanating from the same source material e.g. block 750 should therefore bear resemblance to each other due to the transition of common grain boundaries, crystal defect or impurity rich regions and the like across the saw cut and indeed through the block. During photovoltaic processing, the wafers 701-704 are then extracted from the cassette for processing also in order (701 to 704), or reverse order of cut (704 to 701). Due to these structural similarities, the present inventors further consider that the similarities between wafers in the cassette may be used to provide an alternate approach to testing for process induced faults, either independently, or in combination with the approach already described above.

Figure 8:
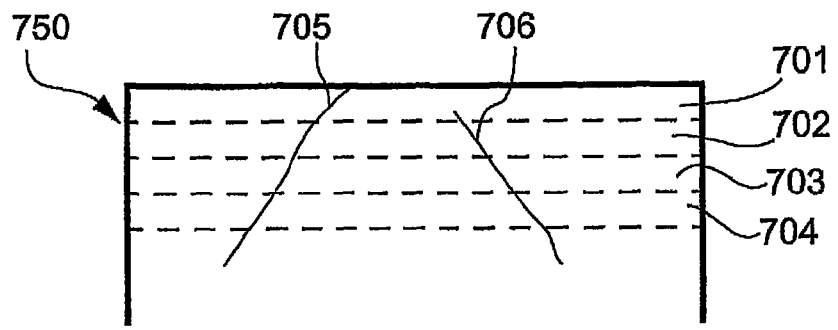
FIG. 8 shows the cutting of consecutive adjacent wafers from a block.

FIG. 8 shows the block 750 from which individual and consecutive wafers 701, 702, 703 and 704 are to be adjacently cut. Although greatly exaggerated for the purposes of illustration, it will be appreciated that structures, such as crystal grain boundaries 705 and 706, traverse through what is to become the wafers 701-704 in substantially the same location. Using this substantial similarity between adjacent and near adjacent wafers, the present inventors propose that such a degree of similarity between such adjacent wafers be used not only to enable the measurement of the growth or incidence of process induced faults in photovoltaic cell processing but also to classify wafers into families ie emanating from the same source material.

The present inventors further propose that since process induced faults typically affect a small fraction of the area of a given wafer, the broad features of a distribution of the spatially correlated differences between adjacent wafers, and sometimes between near-adjacent wafers, are dominated by the structural similarity of the wafers, not by process induced defects. Using this dominance by the structural similarity of the adjacent or near-adjacent wafers, the present inventors propose that a separate indicator of the "electrical structure similarity" of the (near) adjacent wafers can be measured using luminescence imaging which, further, provides an indicator of the reliability of the measurement of the growth or incidence of process induced faults in photovoltaic cell processing based on comparison of luminescence images of (near) adjacent wafers. From the description to follow, it will be appreciated that the process applied to adjacent (consecutive) wafers, can also be applied to near-adjacent (near-consecutive) wafers (eg. wafers 701 and 703) and henceforth, unless expressly mentioned to the contrary, shall be referred to as adjacent or consecutive wafers.

In a fourth aspect, the present invention provides a method classifying semiconductor material samples, said method comprising:

obtaining a plurality of images of samples of the semiconductor material, comparing at least two of the images to provide a measure of electrical structure similarity of the semiconductor material samples, such that semiconductor material samples having a predetermined level of electrical structure similarity are classified as coming from the same family.

As will be discussed below such a process is also suitable for identifying a so called "family" of wafers which emanate from the same source material.

Such a method may be applied prior to or during the manufacturing process of a photovoltaic device. The method is suitable for various samples of the semiconductor material including silicon wafer, or when the material is contained within or processed to become a photovoltaic cell or module.

As discussed above the images are preferably luminescence images. The electrical structure used to determine similarity is selected from the group consisting of edges, lines, grain boundaries and dislocation lines.

In a fifth aspect, the present invention provides a method of classifying semi-conductor material comprising determining the electrical characteristics of a sample of semi-conductor material by obtaining an image of said sample comparing respective obtained images of a plurality of semi-conductor samples analysing said comparison to determine the similarity of said electrical characteristics of said samples to thereby permit grouping into families those samples which fall within a predetermined variation of said electrical characteristics.

This process is suitable for samples of various semiconductor materials including wafers, rhythm wafers, blocks, thin films, photovoltaic cells or photovoltaic modules.

The process is suitable for samples which emanate from the same source or which emanate from different sources.

Additionally, the samples which are grouped into the same family may undergo further processing to determine unique features including electrical, mechanical or cosmetic irregularities of the samples. In some cases, such unique features may include a fault eg. a crack, shunt or contamination of the sample.

Figure 10:
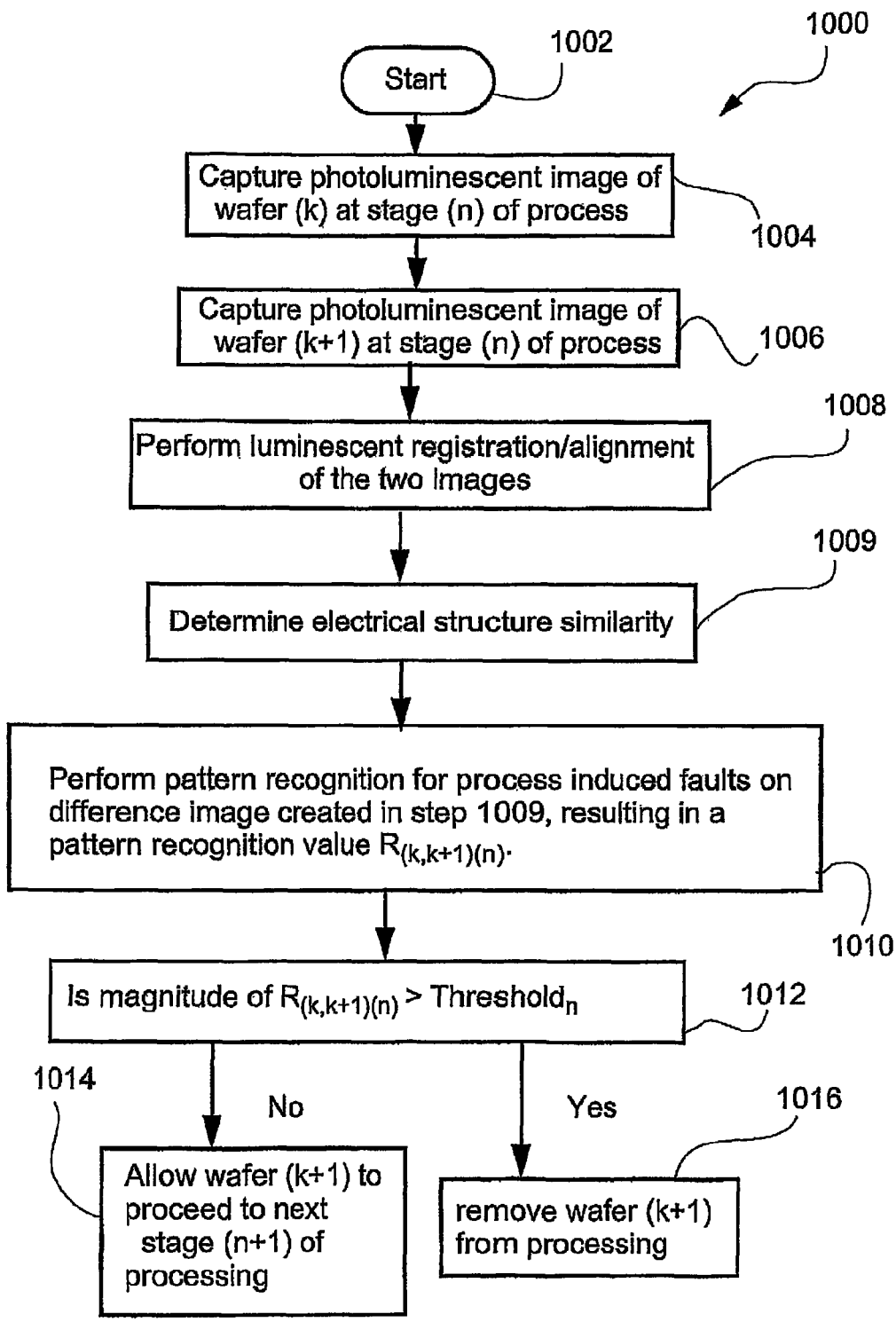
FIG. 10 is a flowchart of an alternate image processing method according to the present disclosure for a single stage of wafer processing.

With reference to FIG. 10, the present method 1000 of wafer examination may be implemented using the PL imaging devices and structure shown in FIG. 3 and described above. More specifically, the method 1000 can be performed at each or any stage of the processing 310 using the imaging devices 331-336, the image capture controller 340, the image repository and processor 342, and the discard process controller 348, when suitable programmed according to the method 1000 of FIG. 10. The method 1000 starts with an entry step 1002 after which step 1004 captures an image of a wafer (k) at stage (n) of the process 310. Step 1006 then captures an image of the next consecutive wafer (k+1) at stage (n) of the process 310.

Figure 9:
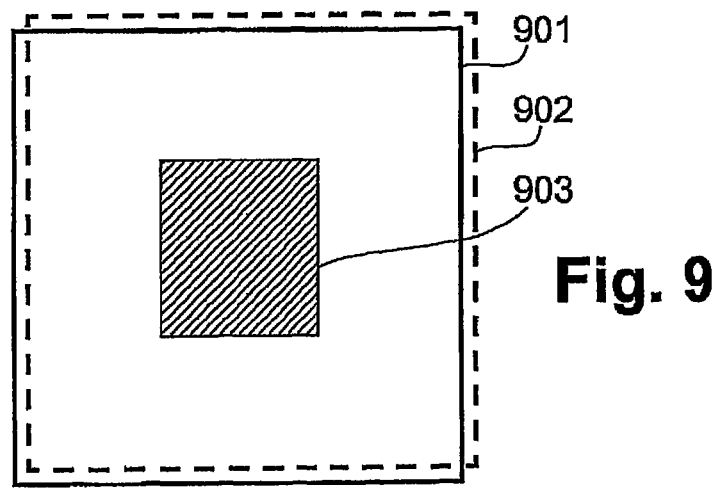
FIG. 9 illustrates the mis-alignment between of images of adjacent wafers.

When imaging wafers to assess electrical structure similarity and/or to calculate difference images, the images should be registered (i.e. aligned) to take account of any misalignment of the wafers in the process. FIG. 9 shows how two wafer images 901 and 902 may be misaligned. Image registration involves "aligning" the two images based on the relative three dimensional position and orientation of the samples in each image, caused by imperfect manual or automated placement of the samples. Alternatively, the size and/or shape of the wafers may be somewhat different, meaning that the regions of "electrical structure similarity" of interest in this method may occur at somewhat different internal positions in each wafer, relative to one or more external boundary of each wafer. The "aligning" process of step 1008 calculates two new images, in which one or both of the original images are transformed, based on the measured or calculated relative three dimensional position and orientation of the samples, or regions of "electrical structure similarity" in the two images. The transformation may be a simple translation of the image by an integral number of pixels, or an interpolation scheme may be used in the image transformation. Image registration may be carried out using optical inspection of the wafer boundaries, or with another suitable approach. In a preferred implementation of step 1008, image registration is achieved using a self-consistent method based on the luminescence images of wafer(k) and wafer(k+1), resulting in several outputs: the optimised image transformation variables, the transformed (registered) images, a "difference" image, a histogram of the "difference" image and a measure of the width of the histogram, for example the FWHM (Full-Width Half-Maximum). The details of step 1008 are described separately in the method 1100 of FIG. 11.

Figure 12:
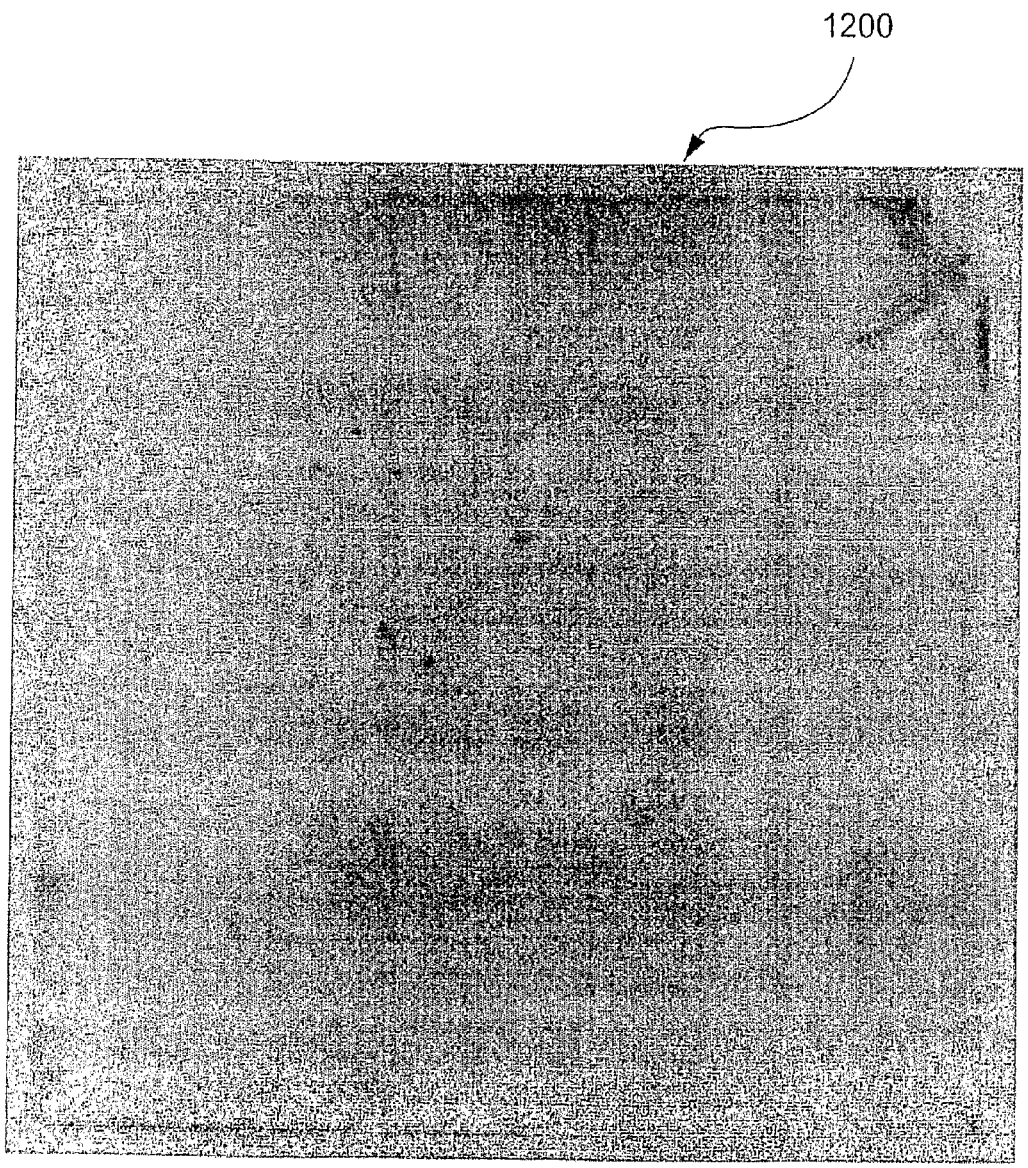
FIGS. 12, 14, 16, 17, 18, and 19 are images relating to wafers.
Figure 13:
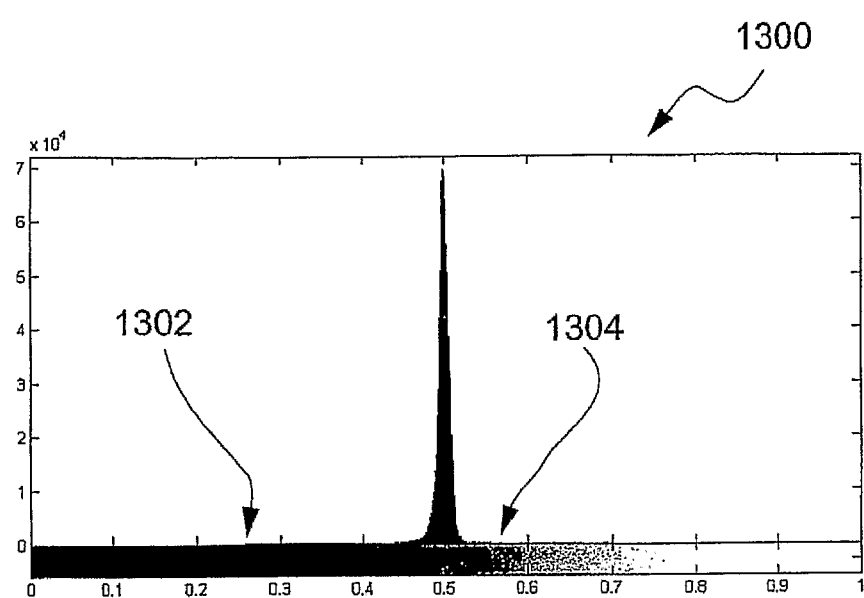
FIGS. 13, 15 and 20 are histograms derived from those images and used to assess the "electrical structure similarity" between wafers.

Normally, in a simple production process, converting block, to wafers, the wafers (k) in step 1004 and (k+1) in step 1006 are adjacent wafers cut from the same block, however step 1009 allows the degree of "electrical structure similarity" to be quantitatively determined, to test if the wafers are, for example, not adjacent or near adjacent or indeed from the same "family" ie. emanating from the same source material, or otherwise not suitable for the reliable determination of process induced defects. In step 1009, the measure of the width of the histogram determined in step 1008 is used to determine the likely reliability of the determination of a measure of process induced defects, including cracks, in subsequent steps. Experiments conducted by the present inventors have indicated that, for wafers having passed through step 4 of the method 300 (ie. the "Silicon Nitride Deposition" step) having nominal dimensions of 15 cm×15 cm×0.02 cm, an typical value of the FWHM of the histogram of the "difference" image (a measure inversely related to the "electrical structure similarity") was about 0.008 normalised units (i.e. where the initial luminescence images and subsequent "difference" image are normalised to unity as described in method 1100). Such "electrical structure similarity" of the wafers shows that these wafers are adjacent, near adjacent or at least came from the same "family" ie. they are produced from the same source material. With such electrical structure similarity this information can be "subtracted" from the comparison between the wafers. Using wafers with this level of "electrical structure similarity", experiments showed that cracks and a shunt, deliberately introduced, were clearly visible on the "difference" image and therefore suitable for detection by suitable pattern recognition algorithms. The experimental data is described below. FIG. 12 shows a "difference image" 1200 prior to the deliberate introduction of cracks and a shunt. FIG. 13 shows a histogram 1300 of the "difference image" 1200 of FIG. 12. The histogram 1300 uses normalised luminance as the x-axis, and a count of the number of pixels in the image for the luminance as the y-axis.

Figure 14:
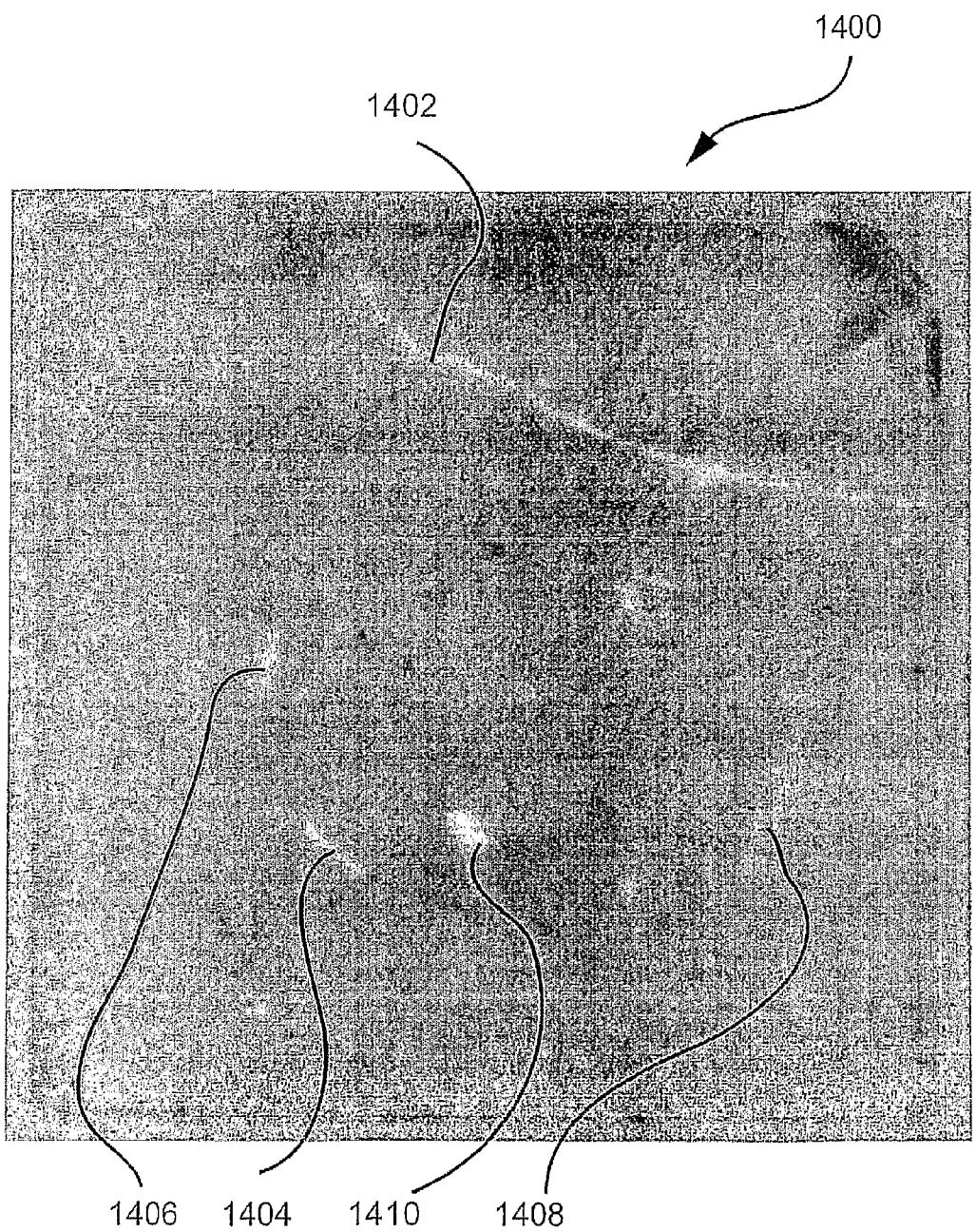
Figure 15:
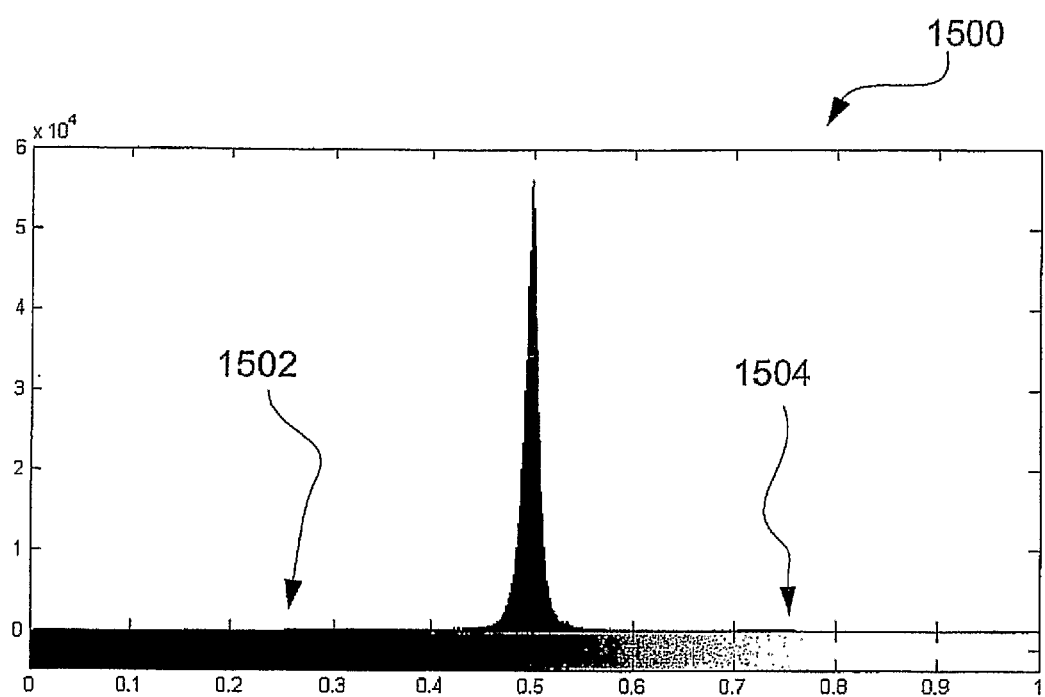
Figure 16:
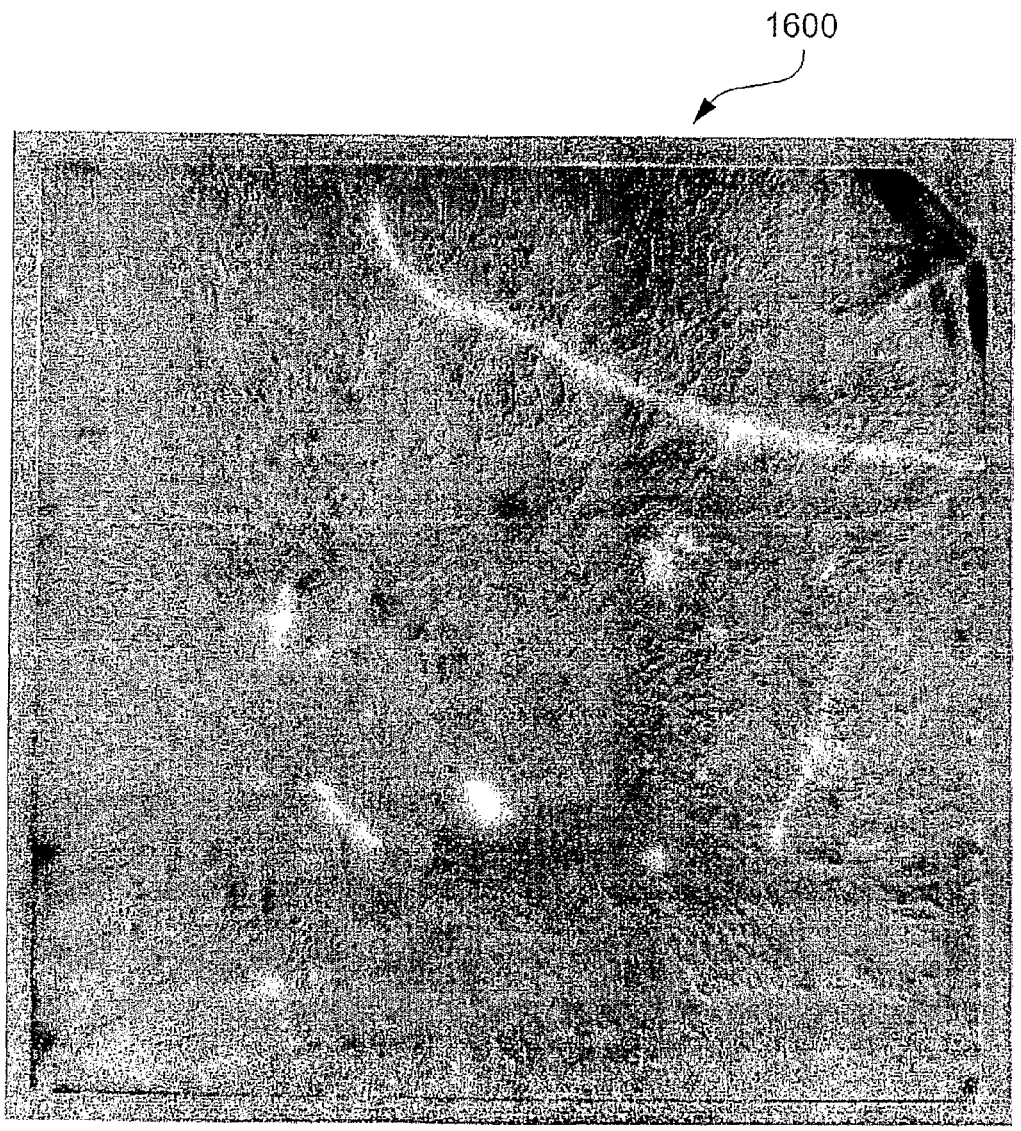
Figure 17:
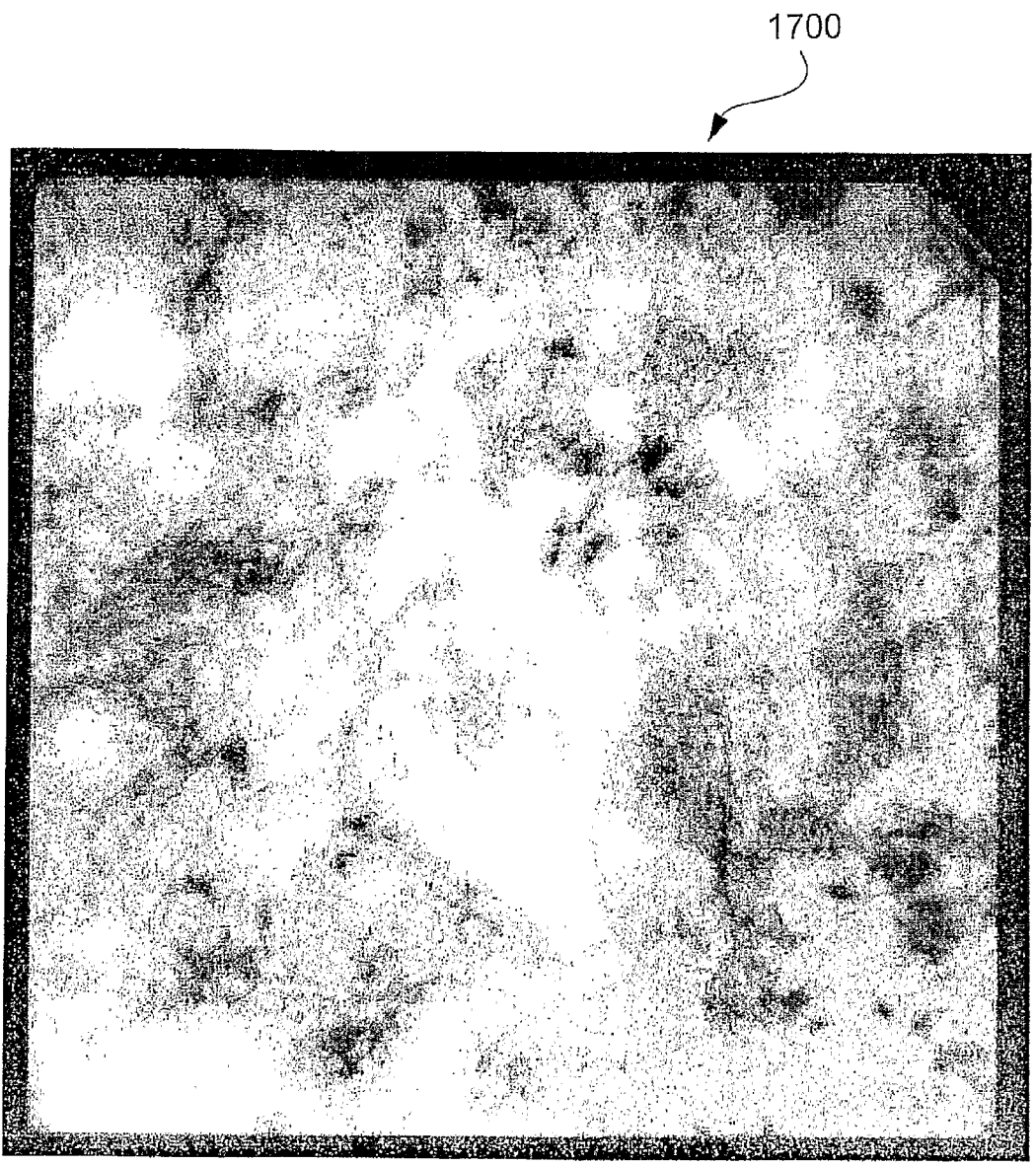
Figure 18:
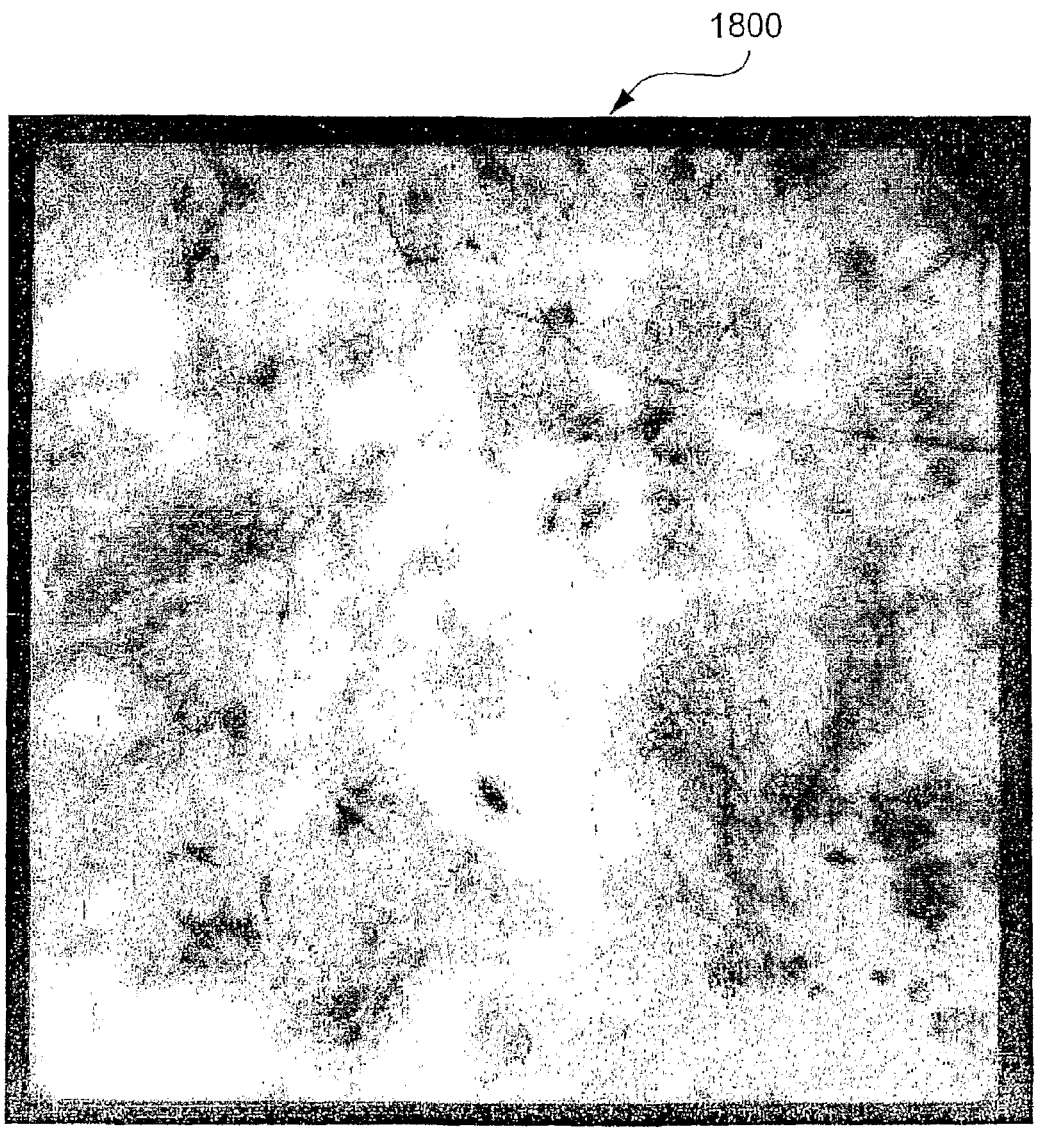
Figure 19:
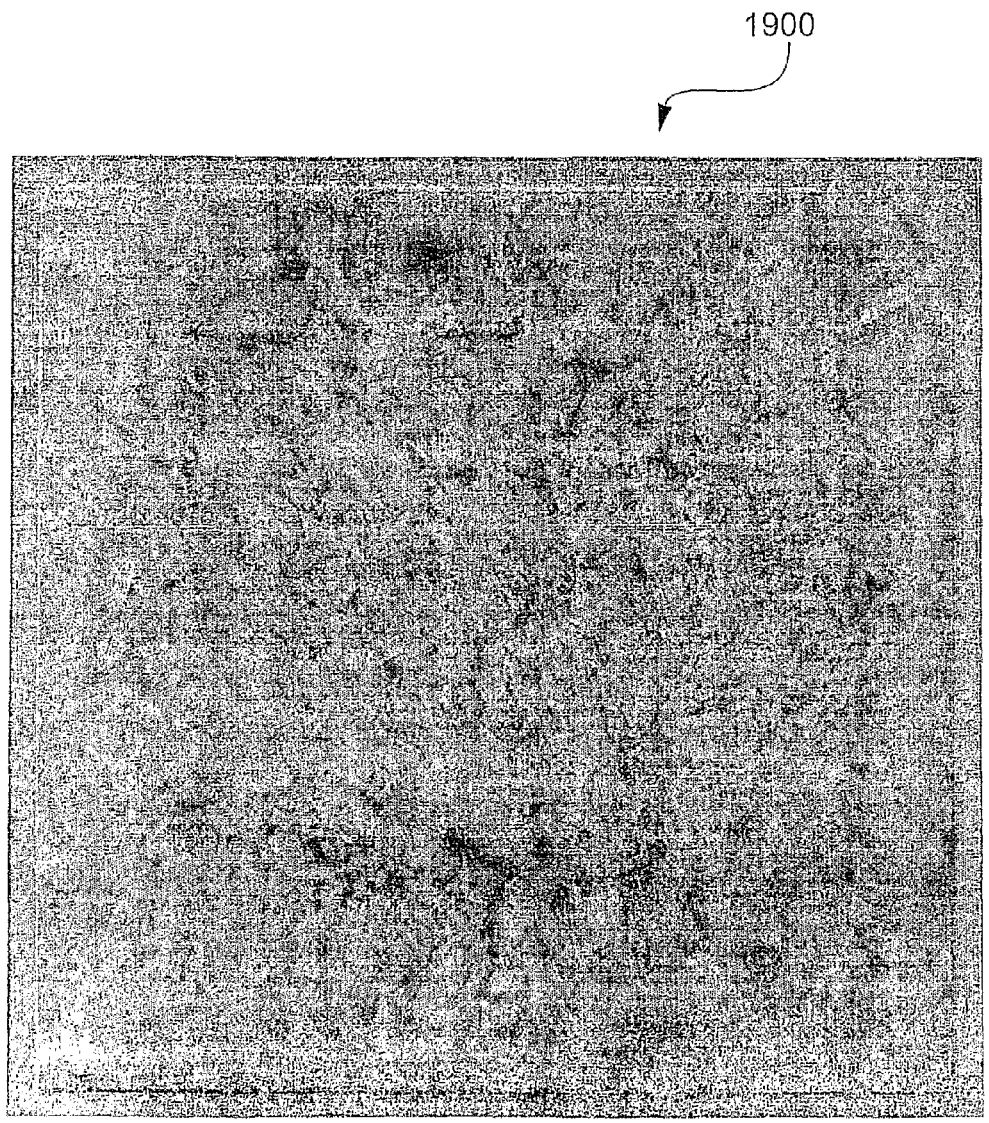
Figure 20:
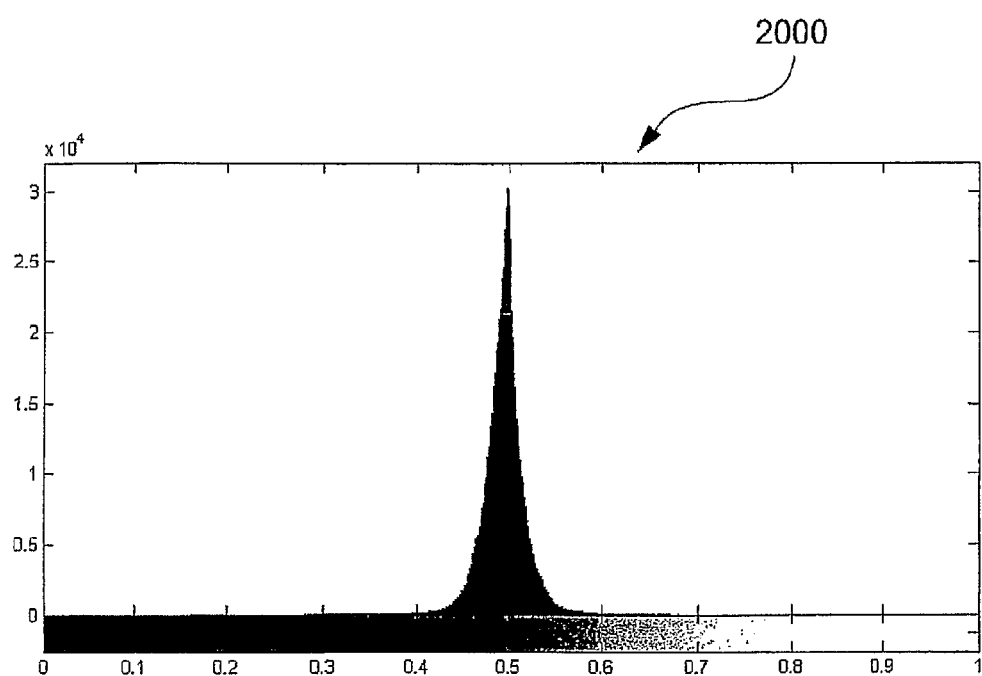

FIG. 14 shows a "difference image" 1400 after the deliberate introduction of cracks 1402, 1404, 1406, 1408 (for example) and a shunt 1410. FIG. 15 shows a histogram 1500 of the "difference image" 1400 of FIG. 14. FIG. 16 is a higher contrast version 1600 of the image 1400 of FIG. 14. FIGS. 17 and 18 are normalised luminescence images 1700 and 1800 of the one wafer (from the pair of wafers) subject to deliberate cracking and shunting, before and after respectively. Both wafers were damaged in the right hand top corner prior to the experiment. Because the damage was not identical, this shows up very dramatically in the "difference" images (FIGS. 12, 14 and 16). The histogram 1300 of FIG. 13 has a long tail 1302 to the left side (black side of the image grey scale) due to the top right corner damage. The histogram 1500 of FIG. 15 shows a more symmetric shape—having a corresponding long left tail 1502 and where the cracked and shunted regions have added a tail 1504 to the right hand side (white side of the image grey scale). The clear human visual recognition of the cracks and shunt in FIGS. 14 and 16 is reflected in the fact that the right hand side tail area 1504 of the histogram 1500 in FIG. 15 was blank 1304 in FIG. 13. It is significant that the FWHM of the histograms in FIGS. 13 and 15 are very similar: 0.008 and 0.007 normalised units (i.e. where the greyscale from black to white covers the numerical range 0.0 to 1.0). The small change is due to the small relative area taken up by cracked and shunted regions. This is important since it means that if a relatively large FWHM is measured, this is highly unlikely to be a result of process induced defects but rather because the pair of wafers being compared are not "adjacent", "near adjacent" or from the same source material. In other words, the wafers are otherwise of relatively low "electrical structure similarity". An example of a difference image 1900 and a histogram 2000 of such a pair is shown in FIGS. 19 and 20 respectively. The FWHM of the histogram 2000 in FIG. 20 is 0.025 normalised units (i.e. where the greyscale from black to white covers the numerical range 0.0 to 1.0). Inspection of the separate luminescence images of the pair shows that they are most likely from similar locations in the block, but are not adjacent wafers.

These results suggest that for the FWHM of about 0.008 or less, detection of process induced defects, in particular cracks, using the method 1000 is likely to be relatively reliable, whereas for FWHM of about 0.025 or higher, the reliability of such detection is likely to be significantly degraded. It will be noted that such a reliability measurement can be conducted by other techniques e.g. gaussian analysis. The process is "beneficial" since it provides a reliability measure of the fault at detection.

According to this alternate method, once the images of adjacent wafers are registered in step 1008 and the "difference" image is assessed in step 1009 to confirm electrical structural similarity, pattern recognition and/or other methods such as threshold tests may be carried out on the difference image and/or the histograms in step 1010 to establish a measure of process induced defects, including cracks. Because the wafers are typically formed of multicrystalline silicon, the "electrical structure similarity" will not be "perfect" and some false positive and false negative results from the method 1000 is to be expected. That degree of these errors will depend upon, at least, the thickness of the wafers, the thickness of the saw cut that separated the wafers, the part of the ingot the wafers are from, and the step in the photovoltaic manufacturing process at which the measurements are carried out. Further experiments, may allow, depending upon the stage (n) of processing, an associated threshold value to be established, permitting comparison between the recognition values $R_{(k,k+1)\cdot(n)}$ and a predetermined threshold, as seen in step 1012.

Where the threshold of the pattern recognition value is exceeded, the wafer (k+1) is presumed to be faulty and may then be removed from the processing at step 1016. If the threshold is not exceeded, the wafer (k+1) is presumed to be good and allowed to the next stage (n+1) of processing at step 1014. Note that once a wafer is removed from processing, such may well upset the extent to which this alternate method can be used for an adjacent wafer. However, based on the presumption that wafer (k) is good, from its own preceding test, then wafer (k) or wafer (k+1) may be compared against the next wafer (k+2), as a near-adjacent wafer, presuming some amount of electrical structure similarity. In some cases the wafers (k+n) can also be tested using this process. Where the similarity test (FIG. 11) fails, the pattern recognition test of FIG. 10 cannot be applied between that pair of wafers.

The different stages of photovoltaic processing may result in markedly different measures of electrical structure similarity and therefore the same form of electrical structure similarity determination need not apply to more than one stage. Where they are used, different values of electrical structure similarity apply.

In the described examples, where a wafer is detected to contain a fault that exceeds a certain value, that wafer is described as being discarded. As an alternative to final discarding, the wafer may be removed from the processing 310 and redirected to a more thorough investigation using alternate methods. Where the wafer is deemed acceptable following such further investigation, it may then be re-introduced into the processing 310. Note that if reintroduced, then the alternate processing of FIG. 10 may not able to be used as such relies upon physically "adjacent" or "family related" wafers preferably being processed consecutively or near consecutively.

Figure 11:
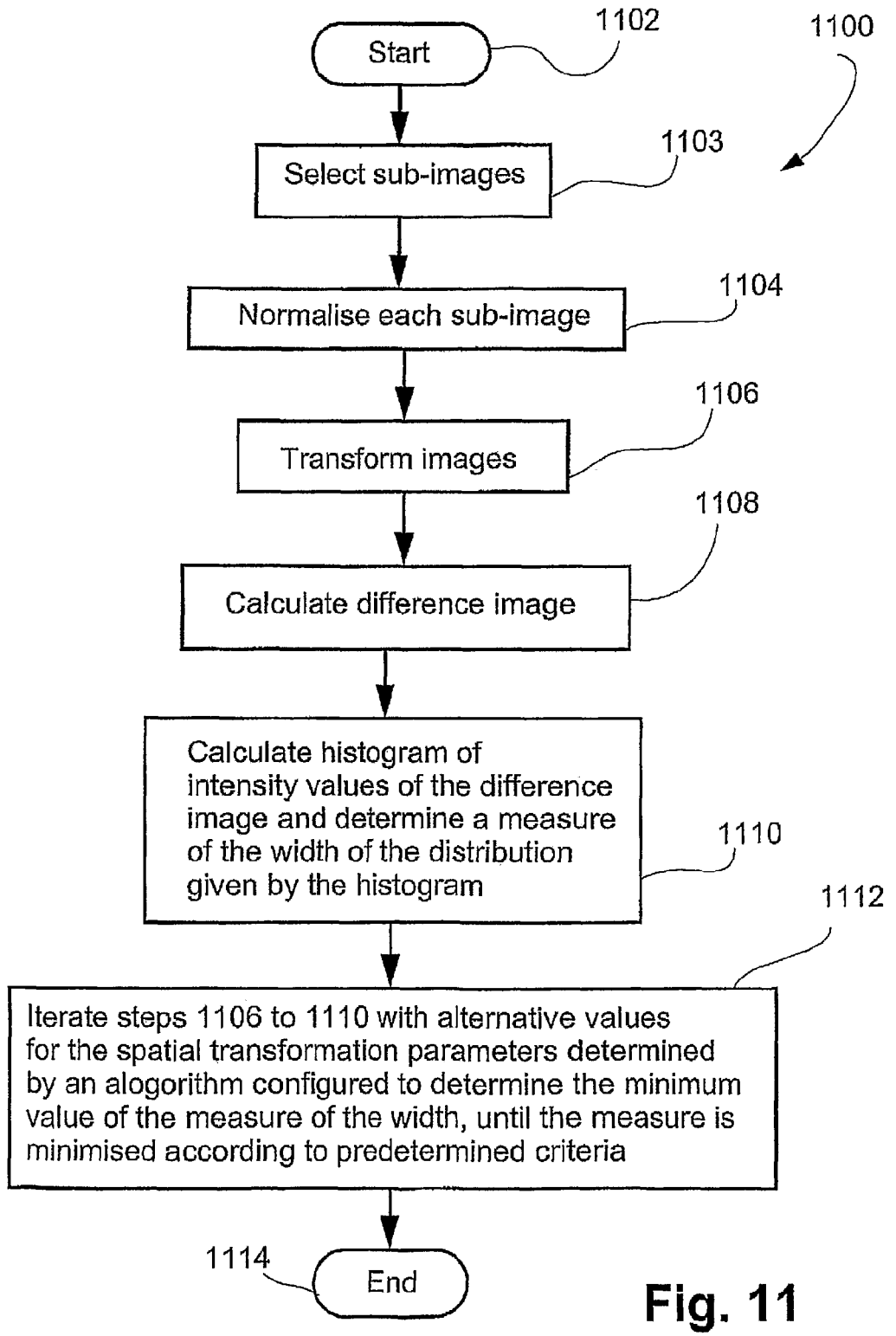
FIG. 11 is a flowchart of a method for implementing step 1008 of FIG. 10.

FIG. 11 shows an iterative method 1100 that may be used to perform the alignment step 1008. In step 1102 the method begins. In step 1103 sub-images are chosen from an identical portion of each image. FIG. 9 shows such a portion 903 of the image 901. The "sub-image" portion chosen may in fact be equal to the entire image, but it may be advantageous to restrict the sub-image to a region within the boundary of the sample, to reduce error in the method due to sample edge and sample-stage effects. Reducing the size of the sub-image advantageously reduces the computational time required to execute the method 1100. If too small a sub-image is chosen, the accuracy of the method 1100 declines. In step 1104 each (sub) image is normalized. For example each image may be normalised to unity in the case that the data is represented as real numbers.

Steps 1106 to 1110 form an iterative loop. The first time that step 1106 is executed, it transforms one or both of the luminescence images into new images using image transformation variables based on an initial estimate or guess of the relative three dimensional position and orientation of the samples, or regions of "electrical structure similarity" in the two images. A typical guess would be that the three dimensional position and orientation of the samples, or regions of "electrical structure similarity" in the two images, is identical. In that case no transformation is required. In subsequent iterations of the method 1100, the value for the relative three dimensional position and orientation of the samples, or regions of "electrical structure similarity" in the two images, is taken from step 1112 (to be described below).

In step 1108, a "difference" image is calculated based on subtraction of the luminescence images of wafer(k) and wafer (k+1). The difference image is desirably restricted to the overlapping regions of the two transformed images.

Optionally, although desirably, normalization of the "difference" image also occurs in step 1108. Continuing the normalisation example from step 1104 above, the image data would be divided by two and then the real number 0.5 added to the image data, resulting in the maximum range of 0.0 to 1.0 in the resulting image data. In the case that the images were identical, all image pixels would have the value 0.5.

Step 1110 calculates a histogram of the image intensity values from the difference image. If the images are sufficiently similar, the histogram will contain a well defined main peak. Continuing the example from step 1108, in the case that the images were identical, the number of counts in the histogram bin containing the real number 0.5 would equal the number of pixels in the "difference" image. The width of the distribution given by the histogram is calculated, using for example the full width at half the maximum height of the distribution (FWHM), or the standard deviation, or another measure. A measure such as FWHM is preferable because it is relatively immune to disproportionate bias from long tails in the distribution which affects the standard deviation for example.

In step 1112, the steps 1106 to 1110 are iterated with alternative values for the spatial transformation parameters determined by an algorithm configured to find the minimum value of the measure of the width, until the measure is minimised according to predetermined criteria. The method 1100 then terminates at step 1114.

The method 1100 may be implemented using a standard numerical minimization routine, for example the function "FMINCON" from the MATLAB program, in conjunction with a separate routine which calculates the histogram width as a function of the image transformation variables and an overall control program.

The arrangements described have particular applicability to photovoltaic cell manufacture using multi-crystalline silicon wafers. This is because cracks are effectively hidden from view amongst the structure in luminescence images arising from numerous regions of poor electrical quality including electrically active grain boundaries, crystal defect or impurity rich regions formed within the multicrystalline wafer. Whilst cracks may be formed in single crystal photovoltaic cell manufacture, such cracks are more readily identifiable. Nevertheless, the arrangements described herein may further be used in single crystal photovoltaic cell manufacture to identify those cracks and to permit discarding of the wafer during the manufacturing process.

Although the arrangements and methods described relate to the photovoltaic cell manufacturing process 310 of FIG. 3, the same principles and similar processes and functionality may also extend to actual photovoltaic module manufacture, where multiple cells are mounted and electrically connected to form a module. The module manufacturing need not be performed at the same facility as wafer/cell processing, provided that relevant image data is supplied to the module manufacturing for correlation with the corresponding cell. Imaging may be performed on individual cells within a module with the images being compared in the manner previously described to provide an assessment of the viability of cells within the module, and thus the module as a whole. Where a cell is found to be faulty, such may then be replaced and the module, or that immediate part of the module, can then be re-tested. Where testing confirms viability of the module, final packing of the module can be performed for shipping.

Where the above description makes reference to one of EL or PL imaging, it will be appreciated that the other, or a combination of both, may be applicable at the relevant stage. Further, the two implementations of process fault detection may be implemented independently or in combination, at distinct processing stages, or at coincident processing stages.

INDUSTRIAL APPLICABILITY

The arrangements described are applicable at least to the manufacture of silicon photovoltaic cell using either single crystal or multi-crystal silicon, most particularly the latter. The arrangements described may also find application to semiconductor photovoltaic cell manufacture using base materials other than silicon, such as silicon germanium, or heterojunction cells (formed by two different materials, such as silicon and amorphous silicon) or tandem cells (consisting of two types of cells in direct physical contact).

The foregoing describes only some embodiments of the present invention, and modifications and/or changes can be made thereto without departing from the scope and spirit of the invention, the embodiments being illustrative and not restrictive.

The claims defining the invention are as follows:

1. A method of manufacturing at least one semiconductor photovoltaic device, said method comprising the steps of:
   obtaining a plurality of images of at least one semiconductor wafer associated with at least one stage of a semiconductor photovoltaic device manufacturing process;
   comparing at least two of the images to identify the incidence or growth of a fault in the at least one wafer; and
   determining whether such incidence or growth of a fault identified exceeds a predetermined level of acceptability,
   wherein said method further comprises a step of processing each said image to obtain a measure related to an incidence of faults in the wafer,
   and said process further comprises detecting spatial features within the wafer image and comparing spatial feature information from at least two images of the wafer to reveal those spatial features that have developed or changed.

2. A method according to claim 1 wherein said device is a wafer, a photovoltaic cell or a photovoltaic module.

3. A method according to claim 1 wherein said images are luminescence images.

4. A method according to claim 1 wherein the incidence or growth of the fault is induced by one or more stages of the manufacturing process from wafer production to module production.

5. A method according to claim 1 wherein when the fault identified exceeds a predetermined level of acceptability, the wafer is discarded, the fault rectified or the wafer is sent to an alternative manufacturing process.

6. A method according to claim 1 wherein said at least one wafer is formed of multicrystalline silicon.

7. A method according to claim 1 wherein said fault comprises one or more of a mechanical, electrical or cosmetic fault in a wafer, photovoltaic cell or photovoltaic module.

8. A method according to claim 7 wherein the fault comprises a crack, shunt, crystal defect or contamination in or of a multicrystalline or monocrystalline silicon wafer.

9. A method according to claim 1 wherein the at least two images are images of a single wafer taken at different positions in the manufacturing process.

10. A method according to claim 9 wherein imaging of the wafer occurs before or after a stage of the manufacturing process.

11. A method according to claim 10 wherein imaging of the wafer occurs before or after a plurality of stages of the manufacturing process.

12. A method according to claim 10 wherein imaging of the wafer occurs before or after at least one of the following stages of the manufacturing process:
   (i) wafer sawing;
   (ii) saw damage etch of the wafer;
   (iii) emitter diffusion;
   (iv) silicon nitride deposition;
   (v) formation of metal contacts on the wafer;
   (vi) thermal treatment of the wafer;
   (vii) edge isolation;
   (viii) electrical testing of a photovoltaic cell produced from the wafer; and
   (ix) one or more stages in the process of incorporating a photovoltaic cell into a photovoltaic module.

13. A method according to claim 1 wherein said spatial features are selected from the group consisting of edges, lines, grain boundaries, dislocation lines and areas of high or low luminescence response.

14. A method according to claim 1 further comprising the step of performing pattern recognition on said images.

15. A method according to claim 1 further comprising determining statistics of fault incidence or growth associated with respective stages of the photovoltaic cell manufacturing process, thereby to assess a level of performance of the respective stage.

16. A method according to claim 1 wherein the at least two images are images taken at a position of the manufacturing process, of two wafers being substantially similar in electrical structure.

17. A method according to claim 16 wherein said wafers originate from the same source material.

18. A method according to claim 17 wherein said wafers are originally adjacent and consecutively derived from said source material.

19. A method according to claim 16 further comprising the steps of:
   (i) aligning at least portions of the images of the wafers;
   (ii) determining a measure of electrical structure similarity of the aligned portions, the measure being substantially independent of the incidence or growth of a fault in the wafers or cells;
   (iii) comparing the measure with a predetermined threshold to establish if the probability of the accurate identification of the incidence or growth of a fault exceeds a predetermined level;
   (iv) generating an analysis image by mathematical operations carried out on the aligned portions, or on greater or lesser parts of the images using the same alignment as used in steps (i) to (iii); and
   (v) identifying the incidence or growth of a fault based on comparison of data from the analysis image with predetermined thresholds or distributions, or pattern recognition performed on the analysis image, or a combination of both comparison of data and pattern recognition.

20. A method according to claim 16 further comprising the steps of:
   (i) aligning at least portions of the images of the wafers;
   (ii) determining a measure of electrical structure similarity of the aligned portions, the measure being substantially independent of the incidence or growth of a fault in the wafers or cells;
   (iii) generating an analysis image by mathematical operations carried out on the aligned portions, or on greater or lesser parts of the images using the same alignment as used in steps (i) to (ii); and
   (iv) identifying the incidence or growth of a process induced fault based on comparison of data from the analysis image with predetermined thresholds or distributions, or pattern recognition performed on the analysis image, or a combination of both comparison of data and pattern recognition;
   (v) calculating the probability that the identification of the fault is accurate using the measure of electrical structure similarity of the aligned portions, the type or size of fault identified and a database, matrix or lookup table relating these quantities; and (vi) comparing the calculated probability with a pre-determined minimum threshold.

21. A method according to claim 19 wherein the step (i) comprises the steps of:
(a) normalising the portions;
(b) spatially transforming one or more of the normalised portions based on predetermined spatial transformation parameters;
(c) determining a difference image from the transformed normalised portions;
(d) calculating a histogram of the intensity values of the difference image and determining a measure of the width of the distribution given by the histogram; and
(e) iterating steps (a) to (d) with alternative values for the spatial transformation parameters determined by an algorithm designed to find the minimum value of the measure of the width, until the measure is minimised according to a predetermined criterion.

22. A method according to claim 20 wherein the step (i) comprises the steps of:
(a) normalising the portions;
(b) spatially transforming one or more of the normalised portions based on predetermined spatial transformation parameters;
(c) determining a difference image from the transformed normalised portions;
(d) calculating a histogram of the intensity values of the difference image and determining a measure of the width of the distribution given by the histogram; and
(e) iterating steps (a) to (d) with alternative values for the spatial transformation parameters determined by an algorithm designed to find the minimum value of the measure of the width, until the measure is minimised according to a predetermined criterion.

23. A method according to claim 19 wherein step (ii) comprises the steps of:
(f) normalising the aligned portions;
(g) obtaining a difference image from the aligned images; and
(h) calculating a histogram of the intensity values of the difference image and determining a measure of the width of the distribution given by the histogram; wherein
the measure of the width of the distribution given by the histogram is inversely related to the electrical structure similarity of the aligned portions.

24. A method according to claim 20 wherein step (ii) comprises the steps of:
(f) normalising the aligned portions;
(g) obtaining a difference image from the aligned images; and
(h) calculating a histogram of the intensity values of the difference image and determining a measure of the width of the distribution given by the histogram; wherein
the measure of the width of the distribution given by the histogram is inversely related to the electrical structure similarity of the aligned portions.

25. A method according to claim 1 wherein at least one of said images comprises a photoluminescence image.

26. A method according to claim 1 wherein at least one of said images comprises an electroluminescence image.

27. A method of analysing a manufacturing process for photovoltaic cells or modules, said process comprising the steps of:
obtaining a plurality of images of at least one semiconductor wafer associated with at least one stage of a semiconductor photovoltaic cell or module manufacturing process;
comparing at least two of the images to identify the incidence or growth of a fault in said at least one wafer at a particular stage of the manufacturing process; and
collating data of fault incidence or growth associated with said stage,
wherein said method further comprises a step of processing each said image to obtain a measure related to an incidence of faults in the wafer,
and said process further comprises detecting spatial features within the wafer image and comparing spatial feature information from at least two images of the wafer to reveal those spatial features that have developed or changed.

28. A method according to claim 27, further comprising the step of applying remedial action to said stage.

29. A manufacturing system for a photovoltaic device having a plurality of stages by which a semiconductor wafer is formed from a source material and processed to form a photovoltaic cell or module, said system comprising:
an imaging apparatus configured to capture a plurality of images of at least one wafer prior to or during said manufacturing process; and
a processor configured to compare and analyse at least two of said images to identify the incidence or growth of a fault in the at least one wafer and to determine whether said fault exceeds a predetermined level of acceptability, wherein the processor is further configured to process each said image to obtain a measure related to an incidence of faults in said at least one wafer, and detect spatial features within the wafer image and compare spatial feature information from at least two images of the wafer to reveal those spatial features that have developed or changed.

30. A manufacturing system according to claim 29 wherein the photovoltaic device is any one of a wafer, photovoltaic cell or photovoltaic module, and said fault comprises one or more of a mechanical, electrical or cosmetic fault.

31. A manufacturing system according to claim 29, further comprising a discard mechanism for removing said device from said manufacturing process if the fault identified exceeds a predetermined level of acceptability.

32. A manufacturing system according to claim 29, wherein said processor is further configured to perform pattern recognition on the at least two images.

33. A manufacturing system according to claim 29, wherein said processor comprises a statistics module for determining statistics of fault incidence or growth associated with respective stages of the photovoltaic device manufacturing process, to thereby assess a level of performance of the respective stage.

34. A manufacturing system for a photovoltaic device having a plurality of stages by which a semiconductor wafer is formed from a source material and processed to form a photovoltaic cell or module, said system comprising:
an imaging apparatus configured to capture a plurality of images of at least one semiconductor wafer associated with at least one stage of a semiconductor photovoltaic cell or module manufacturing process; and
a processor configured to compare at least two of said images to identify the incidence or growth of a fault in the at least one semiconductor wafer at a particular stage of the manufacturing process, and to collate data of fault incidence or growth associated with said stage, wherein the processor is further configured to process each said image to obtain a measure related to an incidence of faults in said at least one wafer, and detect spatial features within the wafer image and compare spatial feature information from at least two images of the wafer to reveal those spatial features that have developed or changed.

35. An article of manufacture comprising a computer usable medium having a computer readable program code configured to conduct the method of claim 1.

36. An article of manufacture comprising a computer usable medium having a computer readable program code configured to conduct the method of claim 27.

37. An article of manufacture comprising a computer usable medium having a computer readable program code configured to operate the system of claim 29.

38. An article of manufacture comprising a computer usable medium having a computer readable program code configured to operate the system of claim 34.

* * * * *